(12) United States Patent
Wei et al.

(10) Patent No.: US 10,220,115 B2
(45) Date of Patent: Mar. 5, 2019

(54) BONE MATRIX COMPOSITIONS HAVING NANOSCALE TEXTURED SURFACES

(71) Applicant: Warsaw Orthopedic, Inc., Warsaw, IN (US)

(72) Inventors: Guobao Wei, Eatontown, NJ (US); Keyvan Behnam, Red Bank, NJ (US); Nanette Forsyth, Bayville, NJ (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 37 days.

(21) Appl. No.: 15/418,351

(22) Filed: Jan. 27, 2017

(65) Prior Publication Data

US 2017/0136149 A1 May 18, 2017

Related U.S. Application Data

(60) Division of application No. 12/267,985, filed on Nov. 10, 2008, now Pat. No. 9,554,920, which is a continuation-in-part of application No. 12/140,062, filed on Jun. 16, 2008, now Pat. No. 8,642,061.

(60) Provisional application No. 60/986,839, filed on Nov. 9, 2007, provisional application No. 60/944,408, filed on Jun. 15, 2007.

(51) Int. Cl.
| | |
|---|---|
| *A61F 2/30* | (2006.01) |
| *A61F 2/46* | (2006.01) |
| *A61L 27/18* | (2006.01) |
| *A61L 27/36* | (2006.01) |
| *A61F 2/28* | (2006.01) |
| *A61L 27/48* | (2006.01) |
| *A61L 27/56* | (2006.01) |
| *A61L 27/24* | (2006.01) |
| *A61L 27/54* | (2006.01) |

(52) U.S. Cl.
CPC ............ *A61L 27/3608* (2013.01); *A61F 2/28* (2013.01); *A61F 2/3094* (2013.01); *A61F 2/4644* (2013.01); *A61L 27/18* (2013.01); *A61L 27/24* (2013.01); *A61L 27/3683* (2013.01); *A61L 27/3687* (2013.01); *A61L 27/48* (2013.01); *A61L 27/54* (2013.01); *A61L 27/56* (2013.01); *A61F 2002/3084* (2013.01); *A61F 2002/4646* (2013.01); *A61L 2300/62* (2013.01); *A61L 2400/12* (2013.01); *A61L 2430/02* (2013.01); *A61L 2430/40* (2013.01)

(58) Field of Classification Search
CPC .................................................. A61L 27/56
USPC .......... 424/484, 486, 488; 435/325; 977/915
See application file for complete search history.

(56) References Cited

U.S. PATENT DOCUMENTS

| | | | |
|---|---|---|---|
| 4,172,128 | A | 10/1979 | Thiele et al. |
| 4,294,753 | A | 10/1981 | Urist |
| 4,394,370 | A | 7/1983 | Jefferies |
| 4,430,760 | A | 2/1984 | Smestad |
| 4,440,370 | A | 4/1984 | Rood |
| 4,440,750 | A | 4/1984 | Glowacki et al. |
| 4,455,256 | A | 6/1984 | Urist |
| 4,472,840 | A | 9/1984 | Jefferies |
| 4,485,097 | A | 11/1984 | Bell |
| 4,563,350 | A | 1/1986 | Nathan et al. |
| 4,619,989 | A | 10/1986 | Urist |
| 4,657,548 | A | 4/1987 | Nichols |
| 4,678,470 | A | 7/1987 | Nashef et al. |
| 4,743,259 | A | 5/1988 | Bolander et al. |
| 4,755,184 | A | 7/1988 | Silverberg |
| 4,761,471 | A | 8/1988 | Urist |
| 4,774,228 | A | 9/1988 | Seyedin et al. |
| 4,774,322 | A | 9/1988 | Seyedin et al. |
| 4,787,906 | A | 11/1988 | Haris |
| 4,789,663 | A | 12/1988 | Wallace et al. |
| 4,789,732 | A | 12/1988 | Urist |
| 4,795,804 | A | 1/1989 | Urist |
| 4,804,744 | A | 2/1989 | Arup |
| 4,810,691 | A | 3/1989 | Seyedin et al. |
| 4,843,063 | A | 6/1989 | Seyedin et al. |
| 4,902,296 | A | 2/1990 | Bolander et al. |
| 5,041,138 | A | 8/1991 | Vacanti et al. |
| 5,073,373 | A | 12/1991 | O'Leary |
| 5,106,748 | A | 4/1992 | Wozney et al. |
| 5,166,187 | A | 11/1992 | Collombel et al. |
| 5,211,664 | A | 5/1993 | Tepic et al. |
| 5,236,456 | A | 8/1993 | O'Leary et al. |
| 5,266,683 | A | 11/1993 | Oppermann et al. |

(Continued)

FOREIGN PATENT DOCUMENTS

| | | |
|---|---|---|
| DE | 2 253 086 | 9/1974 |
| DE | 693 24 117 T2 | 6/1994 |

(Continued)

OTHER PUBLICATIONS

Palin et al. Nanotechnology 16 (2005) 1828-1835. (Year: 2005).*

(Continued)

*Primary Examiner* — Janet L Epps-Smith

(57) ABSTRACT

Bone matrix compositions having nanoscale textured surfaces and methods for their production are provided. In some embodiments, bone matrix is prepared for implantation and retains nanoscale textured surfaces. In other embodiments, nanostructures are imparted to bone matrix wherein collagen fibrils on the surface of the bone matrix have been compromised, thus imparting a nanoscale textured surface to the bone matrix. Generally, these methods may be applied to mineralized or demineralized bone including partially or surface demineralized bone.

7 Claims, 8 Drawing Sheets

(56) References Cited

U.S. PATENT DOCUMENTS

| | | |
|---|---|---|
| 5,270,300 A | 12/1993 | Hunziker |
| 5,284,655 A | 2/1994 | Bogdansky et al. |
| 5,290,558 A | 3/1994 | O'Leary et al. |
| 5,290,763 A | 3/1994 | Poser et al. |
| 5,314,476 A | 5/1994 | Prewett et al. |
| 5,336,264 A | 8/1994 | Constanz et al. |
| 5,354,557 A | 10/1994 | Oppermann et al. |
| 5,378,469 A | 1/1995 | Kemp et al. |
| 5,385,887 A | 1/1995 | Yim et al. |
| 5,405,390 A | 4/1995 | O'Leary et al. |
| 5,490,962 A | 2/1996 | Cima et al. |
| 5,501,706 A | 3/1996 | Arenberg |
| 5,507,813 A | 4/1996 | Dowd et al. |
| 5,518,680 A | 5/1996 | Cima et al. |
| 5,531,735 A | 7/1996 | Thompson |
| 5,563,124 A | 10/1996 | Damien et al. |
| 5,571,189 A | 11/1996 | Kuslich |
| 5,607,269 A | 3/1997 | Dowd et al. |
| 5,618,339 A | 4/1997 | Ito |
| 5,658,882 A | 8/1997 | Celeste et al. |
| 5,723,012 A | 3/1998 | Fages et al. |
| 5,725,579 A | 3/1998 | Fages et al. |
| 5,776,193 A | 7/1998 | Kwan et al. |
| 5,788,959 A | 8/1998 | Singh |
| 5,807,437 A | 9/1998 | Sachs et al. |
| 5,830,493 A | 11/1998 | Yokota et al. |
| 5,846,484 A | 12/1998 | Scarborough et al. |
| 5,877,005 A | 3/1999 | Castor et al. |
| 5,894,070 A | 4/1999 | Hansson et al. |
| 5,899,939 A | 5/1999 | Boyce et al. |
| 5,902,562 A | 5/1999 | Lagasse et al. |
| 5,912,131 A | 6/1999 | Eyre |
| 6,007,580 A | 12/1999 | Lehto et al. |
| 6,018,095 A | 1/2000 | Lerch et al. |
| 6,030,635 A | 2/2000 | Gertzman et al. |
| 6,117,646 A | 9/2000 | Qvist et al. |
| 6,120,558 A | 9/2000 | Poddevin et al. |
| 6,124,273 A | 9/2000 | Drohan et al. |
| 6,143,030 A | 11/2000 | Schroder |
| 6,149,864 A | 11/2000 | Dillow et al. |
| 6,162,258 A | 12/2000 | Scarborough et al. |
| 6,180,606 B1 | 1/2001 | Chen et al. |
| 6,197,325 B1 | 3/2001 | MacPhee et al. |
| 6,217,614 B1 | 4/2001 | Fages et al. |
| 6,245,537 B1 | 6/2001 | Williams et al. |
| 6,294,041 B1 | 9/2001 | Boyce et al. |
| 6,294,187 B1 | 9/2001 | Boyce et al. |
| 6,311,690 B1 | 11/2001 | Jefferies |
| 6,326,018 B1 | 12/2001 | Gertzman et al. |
| 6,352,667 B1 | 3/2002 | English |
| 6,372,257 B1 | 4/2002 | Marchosky |
| 6,387,391 B1 | 5/2002 | Shikinami et al. |
| 6,436,138 B1 | 8/2002 | Dowd et al. |
| 6,440,444 B2 | 8/2002 | Boyce et al. |
| 6,465,168 B1 | 10/2002 | Castor et al. |
| 6,468,543 B1 | 10/2002 | Gilbertson et al. |
| 6,478,825 B1 | 11/2002 | Winterbottom et al. |
| 6,592,886 B1 | 7/2003 | Zimmermann |
| 6,595,998 B2 | 7/2003 | Johnson et al. |
| 6,599,515 B1 | 7/2003 | Delmotte |
| 6,616,698 B2 | 9/2003 | Scarborough |
| 6,618,698 B1 | 9/2003 | Beausoleil et al. |
| 6,623,749 B2 | 9/2003 | Williams et al. |
| 6,648,919 B2 | 11/2003 | Ferree |
| 6,696,073 B2 | 2/2004 | Boyce et al. |
| RE38,522 E | 5/2004 | Gertzman et al. |
| 6,740,093 B2 | 5/2004 | Hochschuler et al. |
| 6,752,831 B2 | 6/2004 | Sybert et al. |
| 6,783,546 B2 | 8/2004 | Zucherman |
| 6,843,807 B1 | 1/2005 | Boyce et al. |
| 6,884,428 B2 | 4/2005 | Binette et al. |
| 6,884,778 B2 | 4/2005 | Jo et al. |
| 6,911,212 B2 | 6/2005 | Gertzman et al. |
| 6,953,594 B2 | 10/2005 | Lee et al. |
| 6,969,404 B2 | 11/2005 | Ferree |
| 6,989,029 B2 | 1/2006 | Bonutti |
| 7,001,390 B2 | 2/2006 | Gebhardt et al. |
| 7,008,591 B2 | 3/2006 | Kafesjian et al. |
| 7,019,192 B2 | 3/2006 | Gertzman et al. |
| 7,025,771 B2 | 4/2006 | Kuslich et al. |
| 7,045,141 B2 | 5/2006 | Merboth et al. |
| 7,060,287 B1 | 6/2006 | Hubbard et al. |
| 7,108,832 B2 | 9/2006 | Christensen et al. |
| 7,163,691 B2 | 1/2007 | Knaack et al. |
| 7,179,299 B2 | 2/2007 | Edwards et al. |
| 7,208,015 B2 | 4/2007 | Pointillart et al. |
| 7,220,282 B2 | 5/2007 | Kuslich |
| 7,226,481 B2 | 6/2007 | Kuslich |
| 7,241,303 B2 | 7/2007 | Reiss et al. |
| 7,261,720 B2 | 8/2007 | Stevens et al. |
| 2001/0031254 A1 | 10/2001 | Bianchi et al. |
| 2001/0043258 A1 | 11/2001 | Ohki |
| 2002/0058947 A1 | 5/2002 | Hochschuler et al. |
| 2002/0068974 A1 | 6/2002 | Kuslich et al. |
| 2002/0077701 A1 | 6/2002 | Kuslich |
| 2002/0133166 A1 | 9/2002 | McKay et al. |
| 2002/0197297 A1 | 12/2002 | Risbud et al. |
| 2003/0008328 A1 | 1/2003 | Wironen et al. |
| 2003/0039676 A1 | 2/2003 | Boyce et al. |
| 2003/0044445 A1 | 3/2003 | Kay et al. |
| 2003/0065392 A1 | 4/2003 | Fan et al. |
| 2003/0072677 A1 | 4/2003 | Kafesjian et al. |
| 2003/0129178 A1 | 7/2003 | Wegman et al. |
| 2003/0143258 A1 | 7/2003 | Knaack et al. |
| 2003/0152548 A1 | 8/2003 | Mikos et al. |
| 2003/0194708 A1 | 10/2003 | Binnerts et al. |
| 2004/0023387 A1 | 2/2004 | John et al. |
| 2004/0024457 A1 | 2/2004 | Boyce et al. |
| 2004/0059364 A1 | 3/2004 | Barton et al. |
| 2004/0072322 A1 | 4/2004 | Thorne |
| 2004/0146543 A1 | 7/2004 | Shimp et al. |
| 2004/0220615 A1 | 11/2004 | Lin |
| 2004/0249464 A1 | 12/2004 | Bindseil et al. |
| 2005/0008620 A1 | 1/2005 | Shimp et al. |
| 2005/0008672 A1 | 1/2005 | Winterbottom et al. |
| 2005/0020506 A1 | 1/2005 | Drapeau et al. |
| 2005/0027033 A1 | 2/2005 | Knaack et al. |
| 2005/0037978 A1 | 2/2005 | Damien |
| 2005/0131417 A1 | 6/2005 | Ahern et al. |
| 2005/0244450 A1 | 11/2005 | Reddi |
| 2005/0244457 A1 | 11/2005 | Reddi |
| 2005/0251267 A1 | 11/2005 | Winterbottom et al. |
| 2005/0283255 A1 | 12/2005 | Geremakis et al. |
| 2006/0216321 A1 | 9/2006 | Lyu et al. |
| 2006/0216323 A1 | 9/2006 | Knaack et al. |
| 2006/0287732 A1 | 12/2006 | Pezeshkian |
| 2007/0073401 A1 | 3/2007 | Pointillart et al. |
| 2007/0093896 A1 | 4/2007 | Malinin |
| 2007/0098756 A1 | 5/2007 | Behnam |
| 2007/0110820 A1 | 5/2007 | Behnam |
| 2007/0118222 A1 | 5/2007 | Lang |
| 2007/0125700 A1 | 6/2007 | Ding et al. |
| 2007/0142916 A1 | 6/2007 | Olson et al. |
| 2007/0154563 A1 | 7/2007 | Behnam et al. |
| 2007/0162132 A1 | 7/2007 | Messerli |
| 2007/0178158 A1 | 8/2007 | Knaack et al. |
| 2007/0231788 A1 | 10/2007 | Behnam et al. |
| 2008/0027546 A1 | 1/2008 | Semler et al. |
| 2008/0033572 A1* | 2/2008 | D'Antonio ............ A61K 35/32 623/23.51 |
| 2008/0069852 A1 | 3/2008 | Shimp et al. |
| 2008/0091270 A1 | 4/2008 | Miller et al. |
| 2008/0152630 A1* | 6/2008 | Ginis .................... A61K 35/28 424/93.7 |
| 2008/0260794 A1 | 10/2008 | Lauritzen et al. |
| 2009/0087471 A1 | 4/2009 | Shimp et al. |
| 2009/0130173 A1 | 5/2009 | Behnam et al. |
| 2009/0155378 A1 | 6/2009 | Behnam et al. |

(56) References Cited

U.S. PATENT DOCUMENTS

| | | |
|---|---|---|
| 2009/0157087 A1 | 6/2009 | Wei et al. |
| 2009/0192474 A1 | 6/2009 | Wei et al. |

FOREIGN PATENT DOCUMENTS

| | | |
|---|---|---|
| EP | 0 082 621 | 6/1983 |
| EP | 0 212 474 | 3/1987 |
| EP | 0 309 241 | 3/1989 |
| EP | 0 148 155 | 4/1989 |
| EP | 0 332 826 A1 | 9/1989 |
| EP | 0 440 991 | 8/1991 |
| EP | 0 567 391 A | 10/1993 |
| EP | 0 603 920 A1 | 6/1994 |
| EP | 0 621 020 A1 | 10/1994 |
| EP | 0781564 A2 | 7/1997 |
| JP | 01/179689 | 7/1989 |
| WO | WO 1988/000205 | 1/1988 |
| WO | WO 1988/001517 | 3/1988 |
| WO | WO 1990/003733 | 4/1990 |
| WO | WO 1994/021298 | 9/1994 |
| WO | WO 1995/031948 | 11/1995 |
| WO | WO 1996/039170 | 12/1996 |
| WO | WO 2000/013615 | 3/2000 |
| WO | WO 2000/045870 | 8/2000 |
| WO | WO 2000/047736 | 8/2000 |
| WO | WO 2001/28461 A2 | 4/2001 |
| WO | WO 2001/70136 A2 | 9/2001 |
| WO | WO 01/79342 A2 | 10/2001 |
| WO | WO 2002/069818 A2 | 9/2002 |
| WO | WO 03/025271 A1 | 3/2003 |
| WO | WO 2003/030956 A3 | 4/2003 |
| WO | WO 2004/073563 A | 9/2004 |
| WO | WO 2005/065396 A2 | 7/2005 |
| WO | WO 2005/072656 A1 | 8/2005 |
| WO | WO 05/081699 A2 | 9/2005 |
| WO | WO 2006/076712 | 7/2006 |
| WO | WO 2007/053850 | 5/2007 |
| WO | WO 2007/133451 | 11/2007 |

OTHER PUBLICATIONS

Fratzl et al. J. Mater. Chem. (2004), 14:2115-2123. (Year: 2004).*
Ou, Wenbin et al. "Effects of Glycerol in the Refolding and Unfolding of Creatine Kinase," *Tsinghua Science and Technology*, 7(4): 352-367 (Aug. 2002).
Ou, Wenbin et al. "Molecular Mechanism for Osmolyte Protection of Creatine Kinase Against Guanidine Denaturation,"*Eur. J. Biochem.*, 268: 5901-5911 (2001).
Landesman, Richard et al., "In Vivo Analysis of the Half-Life of the Osteoinductive Potential of Demineralized Bone Matrix Using Diffusion Chambers", *Calcif. Tissue Int.*, vol. 45, No. 6 1989, 348-353.
Laursen, Malene et al., "Optimal Handling of freshcancellous bone graft-Different peroperative storing techniques evaluated by in vitro osteobalst-like cell metabolism", *Acta Orthop Scand.*, vol. 74, No. 4 2003, 491.
Aspenberg et al., "Monkey Bone Matrix Induces Bone Formation in the Athymic Rat, but Not in Adult Monkeys," *J. of Orthop. Res.* 9:20-25 (1991).
Aspenberg P. et al., "Bone morphogenetic protein induces bone in the squirrel monkey, but bone matrix does not", *Acta Orthop Scand.* 63(6): 619-22 (Dec. 1992).
Blumenthal et al. "The use of collagen membrane barriers in conjunction with combined demineralized bone-collagen gel implants in human infrabony defects," *J. Periodontal* 61(6): 319-327 (Jun. 1990).
Bolander et al.,"The Use of Demineralized Bone Matrix in the Repair of Segmental Defects", *The Journal of Bone and Joint Surgery*, 68-A (8): 1264-1273.
Bravo, D.A. et al., "Accurate and Efficient Cleavage of the Human Insulin Proreceptor by the Human Proprotein-Processing Protease Furin," *Journal Biol Chem.* 269: 25830-25873 (1994).

Cameron, A. et al., "Polyarginines are potent inhibitors," *J. Biol. Chem.* 275: 36741-36749 (2000).
Canalis et al., "Bone morphogenetic proteins, their antagonists, and the skeleton," *Endocrine Rev.* 24(2): 218-235 (2003).
Canalis et al., "Stimulation of DNA and Collagen Synthesis by Autologous Growth Factor in Cultured Fetal Rat Calvaria," *Science*, 210:1021-1023 (1980).
Caplanis et al., "Effect of allogenic freeze-dried demineralized bone matrix on guided tissue regeneration in dogs," *J. Periodontal*, 851-856 (Aug. 1998).
Constantino, et al. "Bone Healing and Bone Substitutes," *Facial Plastic Surgery* 18(1): pp. 14-26 (2002).
Crowe et al., "Inhibition of Enzymatic Digestion of Amylose by Free Fatty Acids in Vitro Contributes to Resistant Starch Formation", *J. Nutr.*, 130(8): 2006-2008 (2000).
Cui et al., "The activity and signaling range of mature BMP-4 is regulated by sequential cleavage at two sites within the prodomain of the precursor," *Genes and Development*, 15:2797-2802 (2001).
Cui et al., "BMP-4 is proteolytically activated by furin and/or PC6 during vertebrae embryonic development," *The Embo Journal*, 17(16):4735-4743 (1998).
Deatherage et al., "Packaging and Delivery of Bone Induction Factors in a Collagenous Implant," *Collagen Rel. Res.* 7:225-231 (1987).
Driessens et al., "Calcium Phosphate Bone Cements," Universitat Politecnica de Catalunya, Barcelona, Spain, 31: 855-77.
Dubois et al., "Evidence that Furin Is an Authentic Transforming Growth Facto-B-1-Converting Enxyme," *American Journal of Pathology*, 158(1):305-316 (2001).
Edwards et al., "Osteoinduction of Human Demineralized Bone: Characterization in a Rat Model," *Clinical Orthopaedics & Rel. Res.*, 357: 219-228 (Dec. 1998).
Elliott, J.C., "Structure and Chemistry of the Apatites and Other Calcium Orthophosphates", Elsevier Science B.V., Amsterdam (1994).
Enlow, Donald H., "Principles of Bone Remodeling: An Account of Post-natal Growth and remodeling Processes in Long Bones and the Mandible," Charles C. Thomas, Springfield, Ill., (1963).
Farley et al., "Human Skeletal Growth Factor: Characterization of the Mitogenic Effect on Bone Cells in Vitro," *Biochem*, 21:3508-3513 (1982).
Flemmig, et al. "Long-Term Maintenance of Alveolar Bone Gain After Implantation of Autolyzed, Antigen-Extracted, Allogenic Bone in Periodontal Intraosseous Defects," *J. Periodontal*, 69(1): 47-53 (Jan. 1998).
Fujishiro, et al. "Histological evaluation of an impacted bone graft substitute composed of a combination of mineralized and demineralized allograft in a sheep vertebral bone defect," *Journal of Biomedical Materials Research Part A*, 538-544 (Aug. 4, 2006).
Gamradt, et al. "Bone Graft for Revision Hip Arthroplasty", *Clin. Ortho. and Related Research*, 417: 183-194 (2003).
Gepstein et al. "Bridging Large Defects in Bone by Demineralized Bone Matrix in the Form of a Powder," *The Journal of Bone and Joint Surgery*, 69A(7): 984-991 (1987).
Glowacki, "Cellular Reactions to Bone-Derived Material," *Clin. Ortho. and Related Research*, 324: 47-54 (1996).
Glowacki et al., "Fate of Mineralized and Demineralized Osseous Implants in Cranial Defects," *Calcif. Tissue Int.*, 33: 71-76 (1981).
Glowacki et al., "Demineralized bone implants," *Symposium on Horizons in Plastic Surgery*, 12(2): 233-41 (1985).
Han B., et al., "Quantitive and sensitive in vitro assay for osteoinductive activity of demineralized bone matrix," *J. Orthop. Res.* 21(4): 648-54 (Jul. 2003).
Han, C. et al. "Autolysed Antigen-Extracted Allogeneic Boen for Repair of Diaphyseal Boen Defects in Rabbits," *Yonsei Medical Journal*, 31(3): 251-257 (1990).
Hollinger, et al. "A comparison of four particulate bone derivatives," *Clin. Ortho. and Related Research*, 267: 255-263 (Jun. 1991).
Hunziker et al., "Repair of Partial Thickness Defects in Articulate Cartilage: Cell Recruitment From the Synovial Membrane", *Journal Bone Joint Surg.*, 78-A: 721-733 (1996).

(56) References Cited

OTHER PUBLICATIONS

Iwata et al. "Chemosterilized Autolyzed Antigen-Extracted Allogeneic (AAA) Bone Matrix Gelatin for Repair of Defects from Excision of Benign Bone Tumors," *Clin. Ortho and Related Research*, 154: 150-155 (1981).
Jain et al., "Anchoring of phospholipase $A_2$. The effect of anions and deuterated water, and the role of N-terminus region," *Biochem. Et Biophys. Acta*, 860: 448-461 (1986).
Janovec, et al. "Autolyzed Antigen-Extracted Allogeneic Bone for Bridging Segmented Diaphyseal Bone Defects in Rabbits," *Clin. Ortho. and Related Research*, 229: 249-256 (Apr. 1988).
Jean et al., "Alpha 1-Antitrypsin Portland, a bioengineered serpin highly selective for furin: Application as an antipathogenic agent", *Proc. Natl. Acad. Sci., USA* 95: 7293-7298 (1998).
Johnson et al. "Human Bone Mortphogenetic Protein Allografting for Reconstruction of Femoral Nonunion," *Clin. Ortho. and Related Research*, 371: 61-74 (2000).
Johnson et al. "Preliminary explorations of reconstructive surgery with implants of autolyzed antigen-extracted allogeneic (AAA) bone supercharged with bone morphogenetic protein (BMP)," *Bone Grafts, Derivatives and Substitutes*, published by Butterworth-Heinemann, Oxford, pp. 363-376 (1994).
Johnson et al. "Resistant Nonunions and Partial or Complete Segmental Defects of Long Bones," *Clin. Ortho. and Related Research*, 277: 229-237 (Apr. 1992).
Kaban et al., "Treatment of Jaw Defects with Demineralized Bone Implants", *Journal of Oral and Maxillofacial Surgery*, pp. 623-626 (Jun. 6, 1989).
Kasten et al., "Comparison of Human Bone Marrow Stromal Cells Seeded on Calcium-Deficient Hydroxyapatite, Betatricalcium Phosphate and Demineralized Bone Matrix", *Biomaterials*, 24(15):2593-603 (2003).
Katz, "The Biology of Heavy Water," *Scientific American*, 106-116 (1960).
Kawai et al., *Clin. Orthopaedics and Related Res.*, 233: 262-267 (1988).
Krysan, D.J., et al., "Quantitative Characterization of Furin Specificity", *Journal Biol. Chem.* 274, pp. 23229-23234 (1999).
Kubler et al. "Allogenic Bone & Cartilage Morphogenesis," *J. Craniomaxillofac. Surg.*, 19(7): 283-288 (1991).
Kubler et al. "Osteoinductive, morphologic, and biomechanical properties of autolyzed, antigen-extracted, allogeneic human bone," *J. Oral Maxillofac Surg*, 51: 1346-1357 (1993).
Kubler et al. "Repair of human skull defects using osteoinductive bone alloimplants," *J. of Cranio Maxillofac. Surg.* 23: 337-346 (1995).
Lee et al., *Nature*, 424: 389 (2003).
Lewandrowski et al., "Flexural Rigidity in Partially Demineralized Diaphyseal Bone Grafts", *Clin, Ortho. Rel. Res.*, 317: 254-262 (1995).
Lewandrowski et al. "Improved Osteoinduction of Cortical Bone Allografts: A Study of the Effects of Laser Perforation and Partial Demineralization" *J. Orthop. Res.* vol., 15(5): 748-756.
Lewandrowski et al. "Kinetics of cortical bone demineralization: Controlled demineralization—A new method for modifying cortical bone allografts", *Journal of Biomedical Materials Research*, vol. 31: 365-372 (1996).
Lewandrowski et al. "Mechanical Properties of Perforated and Partially Demineralized Bone Grafts," *Clin. Ortho. and Related Research*, 353: 238-246 (1998).
Lewandrowski et al., "An Electron Microscopic Study on the Process of Acid Demineralization of Cortical Bone," *Calcified Tissue Int.* 61:294-297 (1997).
Lieberman, et al. "Treatment of Osteonecrosis of the Femoral Head with Core Decompression and Human Bone Morphogenetic Protein," *Clin. Ortho. and Related Research*, 429: 139-145.
Lotz, *Clin. Orthopaedics and Related Res.*, 391S: S108-S115 (2001).
Mellonig, James. "Bone Allografts in Periodontal Therapy," *Clin. Ortho. and Related Research*, 324: 116-125 (1996).
Mellonig, "Decalcified freeze-dried bone allograft as an implant material in human periodontal defects," *The Int'l Journal of Periodontics and Restorative Dentistry*, pp. 41-45 (1984).
Miloslav et al., "Autolyzed antigen-extracted allogeneic bone for bridging segmented diaphyseal bone defects in rabbits," *Clinical Orthopaedics and Related Research*, 229: 249-256 (Apr. 1988).
Nade et al. "Decalcified Bone as a Substrate for Osteogenesis," Bone Joint Surg. 59(2): 189-1996 (1977).
Neigel et al. "Use of Demineralized Bone Implants in Orbital and Craniofacial Reconstruction And Review of the Literature," *Opthal. Plast. Reconst. Surg.*, 12:108 (1996).
Nogami et al., "Sustrata Prepared from Bone Matrix for Chondrogenesis in Tissue Culture", *The Journal of Cell Biology*, 62: 510-519 (1974).
Nogami et al., "Transmembrane Bone Matrix Gelatin -Induced Differentiation of Bone", *Calcif. Tiss. Res.*, 19: 153-163 (1975).
Oberg et al. "Bone formation after implantation of autolysed antigen extracted allogeneic bone In ovariectomized rabbits," *Int. J. Oral Maxillofac.* Surg. 32: 628-632 (2003).
Oberg et al. "Bone healing after implantation of hydroxyapatite granules and blocks (Interpore 200) combined with autolyzed antigen-extracted allogeneic bone and fibrin glue," *Int. J. Oral. Maxillofac. Surg.* 23: 110-114(1994).
"Organic Reactions", vols. 1-40, John Wiley and Sons, New York, NY (1991).
Ousterhout. "Clinical Experience in Cranial and Facial Reconstruction with Demineralized Bone," *Ann. Plast. Surg.* 15(5): 367-373 (1995).
Paralkar et al., "An EP2 receptor-selective prostaglandin $E_2$ agonist induces bone healing," *PNAS*, 100(11): 6736-6740 (2003).
Peel SA et al., "In search of the ideal bone morphogenetic protein delivery system: in vitro studies on demineralized bone matrix, purified, and recombinant bone morphogenetic protein", *J. Craniofac. Surg.*, 14(3): 284-91 (May 2003).
Ray et al., "Bone Implants," *J. Bone Joint Surgery*, 39A(5): 1119-1128 (1957).
Reddi et al., "Biochemical Sequences in the Transformation of Normal Fibroblasts in Adolescent Rats," *Proc. Natl. Acad. Sci. USA*, 69(6): 1601-1605 (1972).
Ripamonti et al. "Bone induction in a composite allogeneic bone/alloplastic implant," *J. Oral Maxillofac. Surg.* 47: 963-969 (1989).
Ripamonti et al. "The induction of bone in osteogenic composites of bone matrix and porous hydroxyapatite replicas: Experimental study on the baboon," *Oral Maxillofac. Surg.* 9: 817-830 (1991).
Ripamonti. "Bone induction in nonhuman primates: an experimental study on the baboon," *Clin. Ortho. and Related Research*, 269: 284-294 (Aug. 1991).
Ripamonti. "Calvarial regeneration in primates with autolyzed antigen-extracted allogeneic bone," *Clin. Ortho. and Related Research*, 282: 293-303 (Sep. 1992).
Rodd, "Chemistry of Carbon Compounds", vols. 1-5 and supplementals, Elsevier Science Publishers, Amsterdan (1989).
Ronningen et al. "Bone formation enhanced by induction," *Acta Orthop Scan* 56: 67-71 (1985).
Ronningen et al. "Osteogenesis promoted by bone matrix combined with marrow," *Acta Orthop Scand* 5Z: 15-18 (1986).
Rosenquist et al. "Effects of bone grafting on maxillary bone healing in the growing pig," *J. Oral Maxillofac.* Surg. 40: 566-569 (1982).
Rosenthal et al. "Demineralized bone implants for nonunion fractures, bone cysts, and fibrous lesions," *Clin. Ortho. and Related Research* 362: 61-69 (1999).
Russell et al., "Clinical Utility of Demineralized Bone Matrix for Osseous Defects, Arthrodesis, and Reconstruction; Impact of Processing Techniques and Study Methodology," *Orthopaedics*, 22(5): 524-531 (May 1999).
Sailer et al. "Application of purified bone morphogenetic protein (BMP) in cranio-maxillo-facial surgery," *Jour. of Cranio-Maxillo-Facial Surgery* 22: 2-11 (1994).
Sambrook, et al. Molecular Cloning: A Laboratory Manual, $3^{rd}$ ed., Cold Spring Harbor Laboratory Press, Cold Spring Harbor (2001).
Sampath and Reddi, "Homology of bone-inductive proteins from human, monkey, bovine, and rat extracellular matrix," *Proc. Nat. Acad. Sci.* 80:6591-6594 (1983).

(56) References Cited

OTHER PUBLICATIONS

Sampath et al., "Bovine osteogenic protein is composed of dimmers of OP-1 and BMP-2A, Two members of the transforming growth factor-beta superfamily," *J. Biol. Chem.*, 5:265(22): pp. 13198-13205 (Aug. 1990).
Sampath et al., "Isolation of osteogenin, an extracellular matrix-associated, bone-inductive protein, by heparin affinity chromatography," *Proc. Natl. Acad. Sci.* 84(7): 7109-7113 (1987).
Schmid et al. "Osteoinduction in tibial defects in the dog," Unfallchirurgie 19: 1-8 (1993).
Schwarz et al., "Dog bone less osteogenetic than rat bone," *Acta. Orthop. Scan.* 60(6): 693-695 (1989).
Schwarz et al. "Decalcified and undecalcified cancellous bone block implants do not heal diaphyseal defects in dogs," *Arch. Orthop. Trauma Surg.* 111:47-50 (1991).
Serini et al., "Class 3 semaphorins control vascular morphogenesis by inhibiting integrin function," *Nature*, 424:391-397 (Jul. 2003).
Smith, Michael et al. "Mar.'s Advanced Organic Chemistry", 5th edition, John Wiley and Sons, New York, NY (Mar. 2001).
Steadman et al., "Microfracture: Surgical Technique and Rehabilitation to Treat Chondral Defects", *Clin. Orthop.*, 391 S:362-369 (2001).
Steiner, D.F., "The proprotein convertases," *Curr. Opinion Chem. Biol.* 2: 31-39 (1998).
Temenoff et al., "Effect of poly(ethylene glycol) molecular weight on tensile and swelling properties of oligo(poly(ethylene glycol) fumarate) hydrogels for cartilage tissue engineering", *OPF Hydrogel Material Properties*, John Wiley & Sons, Inc., pp. 429-437 (2001).
Terashima et al., Chondrogenesis in Outgrowths of Muscle Tissue onto Modified Bone Matrix in Tissue Culture, *Clinical Orthopaedics and Related Research*, 127: 248-256 (Sep. 1977).
Todescan et al., "A Small Animal Model for Investigating Endosseous Dental Implants: Effect of Graft Materials on healing of Endoss, Porous-Surfaced Implants Placed in a Fresh Extraction Socket," *The Journal of Oral and Maxillofacial Implants*, 2(2): 217-223 (1987).
Toriumi et al. "Demineralized Bone," Arch Otolaryngol Head Neck Surg. 116: 676-680 (Jun. 1990).
Ueland et al., *J. Clin. Endocrinol. & Metab.*, 84(1): 123-127 (1999).
Urist. "Bone: Formation by Autoinduction," *Science*, 150(698): pp. 893-899 (1965).
Urist. "The Bone Induction Principle," *Clin. Ortho. Rel. Res.*, 55: 243-283 (1967).
Urist et al., "Bone morphogenesis in Implants of Insoluble Bone Gelatin," *Proc. Natl. Acad. Sci.* 70(12): 3511-5 (Dec. 1973).
Urist et al., ., "Preservation and biodegradation of the morphogenetic property of bone matrix," *J. Theor. Biol.* 38: 155-67 (1973).
Urist et al., "Observations implicating an extracellular enzymic mechanism of control of bone morphogenesis," *J. Histochem & Cytochem*, 22(2): 88-103 (1974).
Urist et al., "A Chemosterilized Antigen-Extracted Autodigested Alloimplant for Bone Banks," *Arch Surg.* vol. 110: 416-428 (Apr. 1975).
Urist et al., "Cartilage Tissue Differentiation from Mesenchymal Cells Derived from Mature Muscle in Tissue Culture", *In Vitro*, 14(8): 697-706 (1978).
Urist et al. "Intertransverse Process Fusion with the Aid of Chemosterilized Autolyzed Antigen-Extracted Allogeneic (AAA) Bone," *Clin. Ortho. and Related Research*, 154: 97-113 (1981).
Urist et al., "Human Bone Morphogenetic Protein (hBMP)," *Proc. Soc. Exp. Biol.* 173:194-199 (1983).
Urist et al., "Purification of bovine bone morphogenetic protein by hydroxyapatite chromatography," *Prop. Natl. Acad. Sci.* 81:371-375 (1984).
Van den Berg et al., "Tissue Engineering, Cells, Scaffolds, and Growth Factors," *Clin. Orthopaedics and Related Res.*, 391S: S244-S250 (2001).
Van den Ouweland, A.M.W. et al., "Structural homology between the human fur gene product and the subtilisin-like protease encoded by yeast KEX2," *Nucl. Acid Res.* 18(3): 664 (1990).
Wang et al., "Purification and characterization of other distinct bone-inducing factors," *Proc. Nat. Acad. Sci.* 85:9484-9488 (1988).
Wang et al., "Recombinant human bone morphogenetic protein induces bone formation," *Proc. Nat. Acad. Sci.* 87:2220-2224 (1990).
White et al., "Effective terminal sterilization using supercritical carbon dioxide," *Journal of Biotechnology*, 123: 504-515 (2006).
Whiteman et al., "Demineralized Bone Powder," *J. Hand. Surg.*, 18B(4): 487-90 (1993).
Whittaker et al., "Matrix Metalloproteinases and Their Inhibitors—Current Status and Future Challenges," *Celltransmissions*, 17(1): 3-14.
Wise, D.L., "Encyclopedia Handbook of Biomaterials and Bioengineering Part B", Applications New York: Marcel Decker (1995).
Xiaobo et al., "Experimental and Clinical Investigations of Human Insoluble Bone Matrix Gelatin," *Clin. Orthopaedics and Related Research*, 293: 360-365 (1993).
Young et al. "Morphological changes of autoclaved autogenic bone implantation and autoclaved autogenic bone supplemented with allogenic demineralized bone matrix in rat parietal bone," *Histol Histopathol.* 11: 361-369 (1996).
Zhang et al., "A Quantitative assessment of osteoinductivity of human demineralized bone matrix," *J. Periodontal*, 68(11): 1076-84 (Nov. 1997).
Glowacki et al., "Fate of Mineralized and Demineralized Osseous Implants in Crania Defects", *Calcified Tissue International*, vol. 33, pp. 8pgs (1981).
Neigel, et al., "Use of Demineralized Bone Implants in Orbital and Craniofacial Reconstruction and a Review of the Literature", *Ophthalmic Plastic and Reconstructive Surgery*, vol. 12, No. 2, pp. 108-120 (1996).
Urist, M., "Bone: Formation by Autoinduction", *Science*, vol. 150, No. 3698, 9pgs. (Nov. 1965).
Urist, et. al., "Bone Induction Principle", *Clinical Orthopaedics and Related Research*, No. 53, pp. 243-283 (Jul.-Aug. 1967).
White, et al., "Effective terminal sterilization using supercritical carbon dioxide", *Journal of Biotechnology*, 123, pp. 504-515 (2006).
Whiteman, et al., "Demineralized Bone Powder", *The Journal of Hand Surgery*, British and European vol. 18B, No. 4, pp. 487-490 (Aug. 1993).
Xiaobo, et al., "Experimental and Clinical Investigations of Human Insoluble Bone Matrix Gelatin", *Clinical Orthopaedics and Related Research*, No. 293, pp. 360-365 (1993).

\* cited by examiner

BONE MATRIX COMPOSITIONS HAVING NANOSCALE TEXTURED SURFACES

CROSS-REFERENCE TO RELATED APPLICATIONS

This application is a divisional application of U.S. patent application Ser. No. 12/267,985 filed Nov. 10, 2008, entitled "BONE MATRIX COMPOSITIONS HAVING NANOSCALE TEXTURED SURFACES," which claims priority to U.S. Provisional Patent Application No. 60/986,839, filed Nov. 9, 2007, and to U.S. Utility patent application Ser. No. 12/140,062, filed Jun. 16, 2008, which claims priority to U.S. Provisional Patent Application No. 60/944,408 filed Jun. 15, 2007, the entire contents of which are hereby incorporated by reference in their entirety.

FIELD OF THE INVENTION

The present invention relates generally to bone matrix compositions and, more specifically, to bone matrix compositions having nanoscale textured surfaces and methods for their production.

BACKGROUND

Overview of Bone Grafts

The rapid and effective repair of bone defects caused by injury, disease, wounds, or surgery is a goal of orthopedic surgery. Toward this end, a number of compositions and materials have been used or proposed for use in the repair of bone defects. The biological, physical, and mechanical properties of the compositions and materials are among the major factors influencing their suitability and performance in various orthopedic applications.

Autologous cancellous bone ("ACB"), also known as autograft or autogenous bone, is considered the gold standard for bone grafts. ACB is osteoinductive and nonimmunogenic, and, by definition, has all of the appropriate structural and functional characteristics appropriate for the particular recipient. Unfortunately, ACB is only available in a limited number of circumstances. Some individuals lack ACB of appropriate dimensions and quality for transplantation, and donor site pain and morbidity can pose serious problems for patients and their physicians.

Much effort has been invested in the identification and development of alternative bone graft materials. Urist published seminal articles on the theory of bone induction and a method for decalcifying bone, i.e., making demineralized bone matrix (DBM). Urist M. R., Bone Formation by Autoinduction, Science 1965; 150(698):893-9; Urist M. R. et al., The Bone Induction Principle, Clin. Orthop. Rel. Res. 53:243-283, 1967. DBM is an osteoinductive material in that it induces bone growth when implanted in an ectopic site of a rodent, at least partially because of the osteoinductive factors contained within the DBM. Honsawek et al. (2000). It is now known that there are numerous osteoinductive factors, e.g., BMP2, BMP4, BMP6, BMP7, which are part of the transforming growth factor-beta (TGF-beta) superfamily. BMP-2 has become the most important and widely studied of the BMP family of proteins. There are also other proteins present in DBM that are not osteoinductive alone but still contribute to bone growth, including fibroblast growth factor-2 (FGF-2), insulin-like growth factor-I and -II (IGF-I and IGF-II), platelet derived growth factor (PDGF), and transforming growth factor-beta 1 (TGF-beta.1).

Accordingly, a known technique for promoting the process of incorporation of osteoimplants is demineralization over outer surfaces, inner surfaces, or the entire volume of the implant. Various methods for demineralizing bone have been discussed. In this regard see, Lewandrowski et al., J. Biomed Materials Res, 31, pp. 365 372 (1996); Lewandrowski et al., Calcified Tiss. Int., 61, pp. 294 297 (1997); Lewandrowski et al., J. Ortho. Res., 15, pp. 748 756 (1997), the contents of each of which is incorporated herein by reference.

DBM implants have been reported to be particularly useful (see, for example, U.S. Pat. Nos. 4,394,370, 4,440,750, 4,485,097, 4,678,470, and 4,743,259; Mulliken et al., Calcif Tissue Int. 33:71, 1981; Neigel et al., Opthal. Plast. Reconstr. Surg. 12:108, 1996; Whiteman et al., J. Hand. Surg. 18B:487, 1993; Xiaobo et al., Clin. Orthop. 293:360, 1993, each of which is incorporated herein by reference). DBM typically is derived from cadavers. The bone is removed aseptically and treated to kill any infectious agents. The bone is particulated by milling or grinding, and then the mineral component is extracted by various methods, such as by soaking the bone in an acidic solution. The remaining matrix is malleable and can be further processed and/or formed and shaped for implantation into a particular site in the recipient. The demineralized bone particles or fibers can be formulated with biocompatible excipients to enhance surgical handling properties and conformability to the defect or surgery site. Demineralized bone prepared in this manner contains a variety of components including proteins, glycoproteins, growth factors, and proteoglycans. Following implantation, the presence of DBM induces cellular recruitment to the site of injury. The recruited cells may eventually differentiate into bone forming cells. Such recruitment of cells leads to an increase in the rate of wound healing and, therefore, to faster recovery for the patient.

BRIEF SUMMARY

Bone matrix compositions and, more specifically, bone matrix compositions having textured surfaces attractive to cells and methods for their production are disclosed.

In some embodiments, nanostructures are imparted to bone matrix compositions wherein the nanofibrous properties on the surface may be compromised. In other embodiments, the bone is processed in a manner so as to expose and/or maintain the nanofibrous structure of the bone. Generally, these methods may be applied to mineralized or demineralized bone including partially or surface demineralized bone. Further, these methods may be applied to particulated or monolithic bone.

In one embodiment, a demineralized bone matrix composition comprising demineralized bone particles exhibiting a nanoscale textured surface wherein the surface includes at least about 60% non-denatured collagen wherein the composition has less than about 6% moisture content is provided.

In one embodiment, a method of drying bone tissue comprising demineralizing the bone and drying the bone tissue in a solvent at its critical point status is provided. In such method, drying using the critical point solvent is done to less than about 6% moisture content.

In yet another embodiment, a method for producing a demineralized bone matrix composition is provided. Bone is provided, the bone is demineralized, the bone is dried such that collagen fibrils on a surface of the bone are compromised, and nanostructures are added to the bone to provide a nanoscale textured surface.

This application refers to various patents, patent applications, journal articles, and other publications, all of which are incorporated herein by reference. The following documents are incorporated herein by reference: U.S. provisional patent application 60/957,614; PCT/US04/43999; PCT/US05/003092; U.S. Pat. No. 7,163,691; PCT/US02/32941; *Current Protocols in Molecular Biology, Current Protocols in Immunology, Current Protocols in Protein Science, and Current Protocols in Cell Biology*, John Wiley & Sons, N.Y., edition as of July 2002; Sambrook, Russell, and Sambrook, *Molecular Cloning: A Laboratory Manual*, 3rd ed., Cold Spring Harbor Laboratory Press, Cold Spring Harbor, 2001; Rodd 1989 "Chemistry of Carbon Compounds," vols. 1-5 and Supps, Elsevier Science Publishers, 1989; "Organic Reactions," volumes 1-40, John Wiley and Sons, New York, N.Y., 1991; March 2001, "Advanced Organic Chemistry," 5th ed. John Wiley and Sons, New York, N.Y. In the event of a conflict between the specification and any of the incorporated references, the specification shall control. Where numerical values herein are expressed as a range, endpoints are included.

While multiple embodiments are disclosed, still other embodiments of the present invention will become apparent to those skilled in the art from the following detailed description. As will be apparent, the invention is capable of modifications in various obvious aspects, all without departing from the spirit and scope of the present invention. Accordingly, the detailed description is to be regarded as illustrative in nature and not restrictive.

BRIEF DESCRIPTION OF THE DRAWINGS

FIG. 5b illustrates the textured surface of demineralized bone matrix of FIG. 5a.

FIG. 6b illustrates textured surface of the demineralized bone matrix of FIG. 6a.

FIG. 7b illustrates the textured surface of the demineralized bone matrix fibers of FIG. 7a.

FIG. 8b illustrates the textured surface of the demineralized bone matrix fibers of FIG. 8a.

DEFINITIONS

Figure 1A:
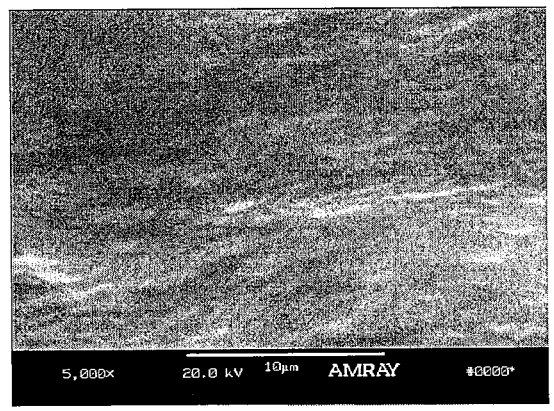
FIG. 1a illustrates the exterior surface of lyophilized demineralized bone matrix as commonly produced in the art.

Bioactive Agent or Bioactive Compound, as used herein, refers to a compound or entity that alters, inhibits, activates, or otherwise affects biological or chemical events. For example, bioactive agents may include, but are not limited to, osteogenic or chondrogenic proteins or peptides, anti-AIDS substances, anti-cancer substances, antibiotics, immunosuppressants, anti-viral substances, enzyme inhibitors, hormones, neurotoxins, opioids, hypnotics, anti-histamines, lubricants, tranquilizers, anti-convulsants, muscle relaxants and anti-Parkinson substances, anti-spasmodics and muscle contractants including channel blockers, mitotics and anti-cholinergics, anti-glaucoma compounds, anti-parasite and/or anti-protozoal compounds, modulators of cell-extracellular matrix interactions including cell growth inhibitors and antiadhesion molecules, vasodilating agents, inhibitors of DNA, RNA or protein synthesis, anti-hypertensives, analgesics, anti-pyretics, steroidal and non-steroidal anti-inflammatory agents, anti-angiogenic factors, angiogenic factors, anti-secretory factors, anticoagulants and/or antithrombotic agents, local anesthetics, ophthalmics, prostaglandins, antidepressants, anti-psychotic substances, anti-emetics, and imaging agents. In certain embodiments, the bioactive agent is a drug. In some embodiments, the bioactive agent is a growth factor, cytokine, extracellular matrix molecule or a fragment or derivative thereof, for example, a cell attachment sequence such as RGD the abbreviation for the amino acid sequence Arginine-Glycine-Aspartic acid. A more complete listing of bioactive agents and specific drugs suitable for use in the present invention may be found in "Pharmaceutical Substances: Syntheses, Patents, Applications" by Axel Kleemann and Jurgen Engel, Thieme Medical Publishing, 1999; the "Merck Index: An Encyclopedia of Chemicals, Drugs, and Biologicals", edited by Susan Budavari et al., CRC Press, 1996; and the United States Pharmacopeia-25/National Formulary-20, published by the United States Pharmcopeial Convention, Inc., Rockville Md., 2001, each of which is incorporated herein by reference.

Biocompatible, as used herein, describes materials that, upon administration in vivo, do not induce undesirable long-term effects.

Bone, as used herein, refers to bone that is cortical, cancellous or cortico-cancellous of autogenous, allogenic, xenogenic, or transgenic origin.

Demineralized, as used herein, refers to any material generated by removing mineral material from tissue, e.g., bone tissue. In certain embodiments, the demineralized compositions described herein include preparations containing less than 5% calcium. In some embodiments, the demineralized compositions may comprise less than 1% calcium by weight. Partially demineralized bone is intended to refer to preparations with greater than 5% calcium by weight but containing less than 100% of the original starting amount of calcium. In some embodiments, demineralized bone has less than 95% of its original mineral content. "Demineralized" is intended to encompass such expressions as "substantially demineralized," "partially demineralized," "surface demineralized," and "fully demineralized." "Partially demineralized" is intended to encompass "surface demineralized."

Demineralized bone matrix (DBM), as used herein, refers to any material generated by removing mineral material from bone tissue. In some embodiments, the DBM compositions as used herein include preparations containing less than 5% calcium and, in some embodiments, less than 1% calcium by weight. In other embodiments, the DBM compositions comprise partially demineralized bone (e.g., preparations with greater than 5% calcium by weight but containing less than 100% of the original starting amount of calcium).

Nanofibers, as used herein, refers generally to fibers of a submicron level. The fibers may generally be any fibers having at least one side or dimension at or below 1000 nanometers. In specific embodiments, the fibers may have at least one side or dimension at or below 100 nanometers.

Nanostructures, as used herein, refers to structures including, at least, nanofibers, nanoparticles, nanospheres, nanopores, nanomicelles, and nano-roughness on surfaces. Nanostructures include structures ranging from approximately 1 nm to approximately 1000 nm in at least one dimension.

Osteoconductive, as used herein, refers to the ability of a substance to serve as a template or substance along which bone may grow.

Osteogenic, as used herein, refers to materials containing living cells capable of differentiation into bone tissue.

Osteoimplant, as used herein, refers to any implant prepared in accordance with the embodiments described herein and therefore may include expressions such as bone membrane, bone graft, etc.

Osteoinductive, as used herein, refers to the quality of being able to recruit cells from the host that have the potential to stimulate new bone formation. Any material that can induce the formation of ectopic bone in the soft tissue of an animal is considered osteoinductive. For example, most osteoinductive materials induce bone formation in athymic rats when assayed according to the method of Edwards et al., "Osteoinduction of Human Demineralized Bone: Characterization in a Rat Model," *Clinical Orthopaedics & Rel. Res.*, 357:219-228, December 1998, incorporated herein by reference. In other instances, osteoinduction is considered to occur through cellular recruitment and induction of the recruited cells to an osteogenic phenotype. Osteoinductivity score refers to a score ranging from 0 to 4 as determined according to the method of Edwards et al. (1998) or an equivalent calibrated test. In the method of Edwards et al., a score of "0" represents no new bone formation; "1" represents 1%-25% of implant involved in new bone formation; "2" represents 26-50% of implant involved in new bone formation; "3" represents 51%-75% of implant involved in new bone formation; and "4" represents >75% of implant involved in new bone formation. In most instances, the score is assessed 28 days after implantation. However, the osteoinductivity score may be obtained at earlier time points such as 7, 14, or 21 days following implantation. In these instances it may be desirable to include a normal DBM control such as DBM powder without a carrier, and if possible, a positive control such as BMP. Occasionally osteoinductivity may also be scored at later time points such as 40, 60, or even 100 days following implantation. Percentage of osteoinductivity refers to an osteoinductivity score at a given time point expressed as a percentage of activity, of a specified reference score. Osteoinductivity may be assessed in an athymic rat or in a human. Generally, as discussed herein, an osteoinductive score is assessed based on osteoinductivity in an athymic rat.

Superficially demineralized, as used herein, refers to bone-derived elements possessing at least about 90 weight percent of their original inorganic mineral content, the expression "partially demineralized" as used herein refers to bone-derived elements possessing from about 8 to about 90 weight percent of their original inorganic mineral content and the expression "fully demineralized" as used herein refers to bone containing less than 8% of its original mineral context.

Textured surface, as used herein, refers to a surface having a nano-scale texture such as containing nanostructures and other attributes.

DETAILED DESCRIPTION

I. Introduction

Bone matrix compositions and, more specifically, bone matrix compositions having nano-scale textured surfaces attractive to cells, and methods for their production are provided. Nano-scale textured surfaces provided on a bone matrix aid in growth factor retention, remodeling, cell attachment, and osteoconductivity of the bone matrix. While specific discussion is made of retaining (throughout processing) and/or imparting textured surfaces, it is to be appreciated that the teachings herein may be applied to non-demineralized bone, partially demineralized bone, or surface demineralized bone. In various embodiments, the nano-scale textured surface may comprise nanofibers, nanoparticles, nanospheres, nanopores, nanomicelles, or other nano-scale structures on a surface of the bone matrix. In embodiments wherein the nanostructures of the textured surface comprise nanofibers, the nanofibers may be oriented. In some embodiments, the nanostructures of the textured surface may be biologically active. For example, the nanostructure may comprise biologically active biomolecules or incorporated with other biological factors such as peptides, growth factors, cytokines, DNA, RNA, siRNA etc.

Bone naturally has a textured surface. Scanning Electron Microcopy (SEM) has facilitated the study of surface morphology in biological applications. The textured surface generally results from fibrillar collagen, the major organic extracellular matrix (ECM) component of bone. The textured surface is thought to be attractive to cells and to facilitate, at least, cell adhesion. The interactions between cells and bone first occur at the surface of the bone. Collagen (type I) is the major component of DBM and is organized in fibrillar bundles in bone. The fibrillar structure of collagen has been demonstrated to be important for cell attachment, proliferation and differentiation. Collagen fiber bundles vary in diameter from 50 to 500 nanometers and the nanometric fibrillar structure of collagen bundles facilitates cellular recognition.

Methods for retaining the nanoscale textured surface of bone while preparing the bone for implantation in accordance with current standards are provided. Methods for imparting a nanoscale textured surface to bone wherein such surface has been compromised or destroyed are also provided.

To prepare bone for implantation, the bone matrix is typically treated to clean, defat, sterilize, virally inactivate, disinfect, demineralize, dehydrate, and/or dry the bone matrix. Reference is made to U.S. Pat. No. 5,846,484, herein incorporated by reference in its entirety, for a description of example treatment of bone intended for implantation. Some treatment processes, while beneficial for some purposes, generally work against conserving or retaining properties of bone. Generally, some of the treatment processes may compromise collagen fibrils on the surface of the bone.

Removal of excess moisture from bone reduces its antigenicity and is done to store and maintain the DBM in active condition for implantation. According to the American Association of Tissue Banks, whole bone containing no more than 6% moisture can be stored at ambient temperatures for up to five years after processing. Typical processes for drying bone include, for example, lyophilization or solvent drying. Typical processes for drying bone such as these, however, generally result in loss of the textured surface of the bone. More specifically, during phase change of the moisture, surface tension of the bone is disturbed. These leads to denaturing of the collagen on the surface of the bone. As a result, dried bone typically exhibits a smooth surface comprising a smear surface of, among other things, denatured collagen fibrils. The collagen fibrils are generally no longer intact and do not retain secondary and tertiary surfaces. Accordingly, the collagen fibrils on the surface of the bone may be considered compromised. The smooth denatured surface does not exhibit the cell attractive qualities as the original nanoscale textured surface of bone.

With specific reference to lyophilization, this process (freeze-drying, i.e., freezing, then sublimation of moisture) is commonly performed on bone to permit its shelf storage for up to several years without spoilage. Lyophilization typically involves freezing whole bone to temperatures as low as −70° C. prior to its packaging and storage. While lyophilization is thought to not disrupt physical properties of bone, it does adversely affect biomechanical properties of the bone as well as the nanoscale texture on the surface of the bone. Lyophilization can result in damage to the bone due to dimensional changes that occur during the freezing and dehydrating operations. The adverse mechanical changes have previously been thought to be associated with structural damage occurring in the bone matrix, such as ultrastructural cracks along the collagen fibers. Examination of lyophilized DBM products has revealed that the nanoscale textured surface of the bone is lost at some point during processing. More specifically, while the bone has nanofibrous interiors, the nanoscale texture of the surfaces of the bone is typically destroyed.

Loss of the nanoscale textured surface of the bone may impact the growth factor retention, remodeling, cell attachment, and osteoconductivity of the bone. Providing a nanoscale textured surface to DBM causes the bone morphology to more closely mimic the natural surface of bone or bone extracellular matrix. In some embodiments, a DBM structure having a biomimetic ECM or having an imparted nanoscale textured surface is provided. In other embodiments, a DBM structure having a nanoscale textured surface maintained during processing for implantation is provided. Providing, or retaining, a nanoscale textured surface on DBM increases the functional surface area of the DBM. Increasing the functional surface area of the DBM provides increased surface area to which proteins may adsorb and cells may attach. Anchorage-dependent cells are cells requiring a solid substratum for growth. Anchorage-dependent cells do not grow, for example, in suspension cultures. With improved cell attachment observed to nanofibrous surfaces, providing a nanoscale textured surface to DBM may affect cell proliferation and differentiation. For example, such surface may enhance cell proliferation and differentiation for anchorage-dependent cells such osteoblast-like cells, pre-osteoblastic cells, and mesenchymal stem cells. Providing a nanoscale textured surface to DBM may affect kinetics and affinity for protein release and binding. Further, it is thought that providing a nanoscale textured surface to DBM may have a positive effect on osteoinductivity.

Bone matrix compositions having a nanoscale textured surface and methods for their production are thus provided. In some embodiments, the bone is processed in a manner so as to expose or maintain the nanofibrous structure of the bone. In some embodiments, the bone matrix has no smear layer or a smear layer of lesser dimensions than would be expected when the bone matrix is processed using lyophilization. In some embodiments, collagen on the surface of the prepared bone exhibits secondary and tertiary surfaces. In other embodiments, nanoscale textured surfaces are imparted to bone matrix compositions wherein the nanoscale textured surface of the bone has been compromised. Generally, these methods may be applied to mineralized or demineralized bone including partially or surface demineralized bone. Further, while specific discussion may be made to particulated bone, it is to be appreciated that the methods disclosed herein may alternatively be applied to monolithic bone.

In some embodiments, biological activities of the bone matrix may be increased. Accordingly, the bone matrix, and compositions formed from the bone matrix, may variously be referred to as biologically active and/or, in some cases, osteoinductive. The biological activities of the bone composition provided herein that may be increased include but are not limited to osteoinductive activity, osteogenic activity, chondrogenic activity, wound healing activity, neurogenic activity, contraction-inducing activity, mitosis-inducing activity, differentiation-inducing activity, chemotactic activity, angiogenic or vasculogenic activity, exocytosis or endocytosis-inducing activity, or other cell or biological activity. It will be appreciated that bone formation processes frequently include a first stage of cartilage formation that creates the basic shape of the bone, which then becomes mineralized (endochondral bone formation). Thus, in many instances, chondrogenesis may be considered an early stage of osteogenesis, though of course it may also occur in other contexts.

II. Providing Demineralized Bone

Bone used in the methods described herein may be autograft, allograft, or xenograft. In various embodiments, the bone may be cortical bone, cancellous bone, or cortico-cancellous bone. While specific discussion is made herein to demineralized bone matrix, bone matrix treated in accordance with the teachings herein may be non-demineralized, demineralized, partially demineralized, or surface demineralized. The following discussion applies to demineralized, partially demineralized, and surface demineralized bone matrix.

Any suitable manner of demineralizing the bone may be used. For example, U.S. Pat. No. 5,405,390, herein incorporated by reference, describes suitable methods. DBM includes the collagen matrix of the bone together with acid insoluble proteins including bone morphogenic proteins (BMPs) and other growth factors. It can be formulated for use as granules, gels, sponge material or putty and can be freeze-dried for storage. Sterilization procedures used to protect from disease transmission may reduce the activity of beneficial growth factors in the DBM. DBM provides an initial osteoconductive matrix and exhibits a degree of osteoinductive potential, inducing the infiltration and differentiation of osteoprogenitor cells from the surrounding tissues.

DBM preparations have been used for many years in orthopedic medicine to promote the formation of bone. For example, DBM has found use in the repair of fractures, in the fusion of vertebrae, in joint replacement surgery, and in treating bone destruction due to underlying disease such as rheumatoid arthritis. DBM is thought to promote bone formation in vivo by osteoconductive and osteoinductive processes. The osteoinductive effect of implanted DBM compositions is thought to result from the presence of active growth factors present on the isolated collagen-based matrix. These factors include members of the TGF-β, IGF, and BMP protein families. Particular examples of osteoinductive factors include TGF-β, IGF-1, IGF-2, BMP-2, BMP-7, parathyroid hormone (PTH), and angiogenic factors. Other osteoinductive factors such as osteocalcin and osteopontin are also likely to be present in DBM preparations as well. There are also likely to be other unnamed or undiscovered osteoinductive factors present in DBM.

In one suitable demineralization procedure, the bone is subjected to an acid demineralization step followed by a defatting/disinfecting step. The bone is immersed in acid to effect demineralization. Acids that can be employed in this step include inorganic acids such as hydrochloric acid and as well as organic acids such as formic acid, acetic acid, peracetic acid, citric acid, propionic acid, etc. The depth of demineralization into the bone surface can be controlled by adjusting the treatment time, temperature of the demineralizing solution, concentration of the demineralizing solution, agitation intensity during treatment, and other applied forces such as vacuum, centrifuge, pressure, and other factors such as known to those skilled in the art. Thus, in various embodiments, the DBM may be fully demineralized, partially demineralized, or surface demineralized.

The demineralized bone is rinsed with sterile water and/or buffered solution(s) to remove residual amounts of acid and thereby raise the pH. A suitable defatting/disinfectant solution is an aqueous solution of ethanol, the ethanol being a good solvent for lipids and the water being a good hydrophilic carrier to enable the solution to penetrate more deeply into the bone particles. The aqueous ethanol solution also disinfects the bone by killing vegetative microorganisms and viruses. Ordinarily, at least about 10 to 40 percent by weight of water (i.e., about 60 to 90 weight percent of defatting agent such as alcohol) is present in the defatting disinfecting solution to produce optimal lipid removal and disinfection within a given period of time. A suitable concentration range of the defatting solution is from about 60 to about 85 weight percent alcohol, or about 70 weight percent alcohol.

In some embodiments, the demineralized bone may be further treated to affect properties of the bone. For example, the DBM may be treated to disrupt the collagen structure of the DBM. Such treatment may comprise collagenase treatment, heat treatment, mechanical treatment, or other. Reference is made to U.S. Provisional Patent Applications 60/944,408, 60/944,417, and 60/957,614, herein incorporated by reference, for further treatment options. In embodiments wherein collagen disruption affects the nanoscale textured surface, such nanoscale textured surface may later be imparted to the bone.

While demineralized bone is specifically discussed herein, in some embodiments, the teachings herein may be applied to non-demineralized bone, to partially demineralized bone, or to surface demineralized bone.

III. Provide Bone Particles

The bone may be particulated. If the bone is demineralized, the bone may be particulated before, during or after demineralization. As previously discussed, in some embodiments, the bone may be monolithic and may not be particulated. Accordingly, while specific discussion is given to particulating bone, the methods disclosed herein and the nanoscale textured surfaces disclosed herein may be used with monolithic bones or implants, including, for example, surface demineralized implants or fully demineralized cortical bone implants.

The bone may be milled and ground or otherwise processed into particles of an appropriate size before or after demineralization. The particles may be particulate or fibrous. The terms milling or grinding are not intended to be limited to production of particles of a specific type and may refer to production of particulate or fibrous particles. In certain embodiments, the particle size may be greater than 75 microns, such as ranging from about 100 to about 3000 microns, or from about 200 to about 2000 microns. After grinding, the bone particles may be sieved to select those particles of a desired size. In certain embodiments, the particles may be sieved though a 50 micron sieve, a 75 micron sieve, or a 100 micron sieve.

IV. Dry Bone Matrix

Figure 1B:
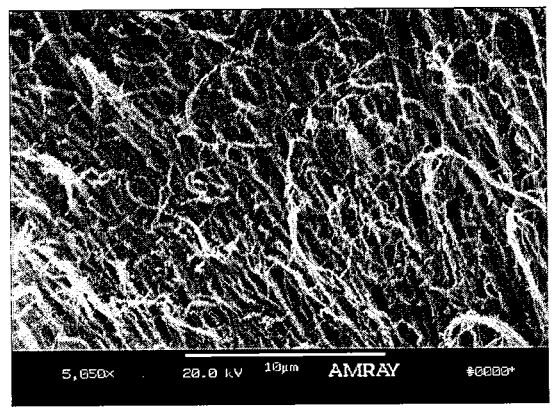
FIG. 1b illustrates the interior of lyophilized demineralized bone matrix as commonly produced in the art.

As previously discussed, DBM typically is dried, for example via lyophilization or solvent drying, to store and maintain the DBM in active condition for implantation. As noted, however, each of these processes is thought to destroy the nanofibrous surface structure of bone. FIGS. 1a and 1b illustrate differences in the smooth exterior surface and the textured interior surface of lyophilized bone matrix. FIG. 1a illustrates the smooth surface of the exterior surface of lyophilized bone matrix while FIG. 1b illustrates the nanofibrous interior surface of lyophilized bone matrix. As may be appreciated, the structural damage of the exterior surface, specifically the loss of the nanofibrous nature of the surface, reduces the overall surface area. Physical alterations to the surface and reduction in surface area can affect cell attachment, mobility, proliferation, and differentiation. The surface's affinity for growth factors and release kinetics of growth factors from the surface may also be altered.

Accordingly, in some embodiments, methods for drying bone to store and maintain the bone in active condition for implantation that maintain a nanoscale textured surface on an exterior surface of the bone are provided. In one embodiment, the bone matrix is treated using critical point drying (CPD) technique, thereby reducing destruction of the nanoscale textured surface of the bone. While specific description is made to critical point drying, it is to be appreciated that, in alternative embodiments, super critical point treatment may be used. In various embodiments utilizing CPD, a percentage of collagen fibrils on the surface of the bone are non-denatured after drying to a residual moisture content of approximately 15% or less. In some embodiments, after drying, the bone matrix has a residual moisture content of approximately 8% or less. In some embodiments, after drying, the bone matrix has a residual moisture content of approximately 6% or less. In some embodiments, after drying, the bone matrix has a residual moisture content of approximately 6% or less. In some embodiments, after drying, the bone matrix has a residual moisture content of approximately 3% or less. In some embodiments, after drying, the bone matrix has a residual moisture content of approximately 1% or less. In some embodiments, approximately 60% or more of the collagen fibrils on the surface of the bone matrix are non-denatured. In some embodiments, approximately 75% or more of the collagen fibrils on the surface of the bone matrix are non-denatured. In some embodiments, approximately 90% or more of the collagen fibrils on the surface of the bone matrix are non-denatured. Collagen fibrils typically range in size from approximately 50 nm to approximately 500 nm. In some embodiments, bone matrices processed using CPD retain a nanoscale texture surface having surface features on the order of approximately 1 nm to approximately 1000 nm. In certain embodiments, bone matrices processed using CPD retain a nanoscale texture surface having surface features on the order of approximately 40 to approximately 600 nm. In other embodiments, bone matrices processed using CPD retain a nanoscale texture surface having surface features on the order of approximately 50 to approximately 500 nm. In some embodiments, nanostructures are imparted to bone matrices processed using CPD and retaining a nanoscale texture surface, thus providing an enhanced nanoscale texture surface on the bone matrix, as described below.

Evaporative drying and freeze drying of specimens can cause deformation and collapse of structures, especially sub-micrometric and nanometric structures. Without wishing to be bound to a particularly theory, this deformation and structure is thought to be caused because, as a substance crosses the boundary from liquid to gas, the substance volatilizes such that the volume of the liquid decreases. As this happens, surface tension at the solid-liquid interface pulls against any structures to which the liquid is attached. Delicate structures, such as the nanofibrous structures of bone surfaces, tend to be broken apart by this surface tension. Such damage may be caused by the effects of surface tension on the liquid/gas interface. Critical point drying is a technique that avoids effects of surface tension on the liquid/gas interface by substantially preventing a liquid/gas interface from developing. Critical point or supercritical drying does not cross any phase boundary, instead passing through the supercritical region, where the distinction between gas and liquid ceases to apply. As a result, materials dried using critical point drying are not exposed to damaging surface tension forces. When the critical point of the liquid is reached, it is possible to pass from liquid to gas without abrupt change in state. Critical point drying can be used with bone matrices to phase change from liquid to dry gas without the effects of surface tension. Accordingly, bone dehydrated using critical point drying can retain at least some of the nanoscale texture on the surface.

In some embodiments, critical point drying is carried out using carbon dioxide. However, other mediums such as freon, including Freon 13 (chlorotrifluoromethane), may be used. Generally, fluids suitable for supercritical drying include carbon dioxide (critical point 304.25 K at 7.39 MPa or 31.1° C. at 1072 psi or 31.2° C. and 73.8 bar) and freon (~300 K at 3.5-4 MPa or 25 to 30° C. at 500-600 psi). Nitrous oxide has similar physical behavior to carbon dioxide, but is a powerful oxidizer in its supercritical state. Supercritical water is also a powerful oxidizer, partly because its critical point occurs at such a high temperature (374° C.) and pressure (3212 psi/647K and 22.064 MPa).

In some embodiments, the bone may be pretreated to remove water prior to critical point drying. Thus, in accordance with one embodiment, bone matrix is dried using carbon dioxide in (or above) its critical point status. After demineralization, bone matrix samples (in water) may be dehydrated to remove residual water content. Such dehydration may be, for example, through a series of graded ethanol solutions (for example, 20%, 50%, 70%, 80%, 90%, 95%, 100% ethanol in deionized water). In some embodiments, penetrating the tissue with a graded series of ethanol solutions or alcohols may be accomplished in an automated fashion. For example, pressure and vacuum could be used to accelerate penetration into the tissue. U.S. Pat. No. 6,162,258 discusses processes for penetrating tissue and is herein incorporated by reference in its entirety. Such solvent drying may be done to an extent wherein the nanoscale textured surface of the bone is not disrupted or such that at least some percentage of collagen fibrils on the surface remain non-denatured.

In alternative embodiments, other means or procedures for removing water (drying or dehydrating) from the bone may be used. For example, the bone may be washed with other dehydrating liquids such as acetone to remove water, exploiting the complete miscibility of these two fluids. The acetone may then washed away with high pressure liquid carbon dioxide.

In some embodiments, the dehydrated bone matrix is placed in a chamber within a critical point drying (CPD) apparatus and flushed with liquid $CO_2$ to remove ethanol (or other dehydrating liquid). Flushing with liquid $CO_2$ may be done one or more times. The temperature and/or pressure are then raised to the critical point (the critical point for $CO_2$ is reached at 31.2° C. and 73.8 bar). To perform critical point drying, the temperature and pressure may continue to be raised, for example to 40° C. with corresponding pressure of 85 bar. Thus, in some embodiments, the liquid carbon dioxide is heated until its pressure is at or above the critical point, at which time the pressure can be gradually released, allowing the gas to escape and leaving a dried product.

Figure 2:
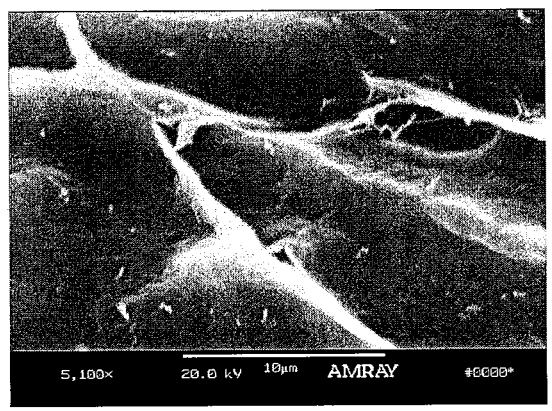
FIG. 2 illustrates the smooth and solid surface of lyophilized demineralized bone matrix fibers.
Figure 3:
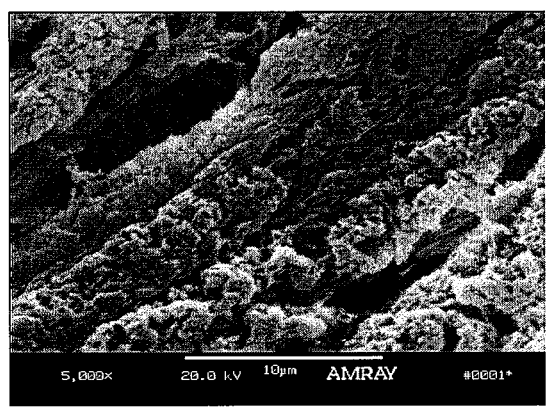
FIG. 3 illustrates the textured surface of critical-point-dried demineralized bone matrix fibers, in accordance with one embodiment.

FIG. 2 illustrates the surface of lyophilized DBM fibers. As shown, the surface is generally smooth and solid. FIG. 3 illustrates the surface of critical point dried DBM fibers, in accordance with one embodiment. As shown, the surface has a nanoscale texture comprising nanofibers and the nanofibers are oriented. DBM dried with critical point carbon dioxide has increased biological activity and osteoinductivity compared to DBM dried with lyophilization.

In a further embodiment, the critical point dried samples may further be treated, or alternatively be treated, with supercritical carbon dioxide (carbon dioxide above the critical point). Supercritical $CO_2$ may also be useful in viral inactivation. In some embodiments, thus, the bone matrix is placed in a supercritical $CO_2$ chamber and liquid $CO_2$ is introduced, for example, by a air pump. The temperature is raised to 105° C. with corresponding pressure about 485 bar. In alternative embodiments, other temperatures and/or pressures above the critical point of $CO_2$ may be used. The samples are soaked in supercritical $CO_2$ for a certain time and $CO_2$ is released. The resulting bone samples retain nanofibrous surface morphologies and osteoinductivity after such treatment.

Figure 5A:
FIG. 5a illustrates demineralized bone matrix wherein the bone has been demineralized, milled in wet conditions, and then critical point dried, in accordance with one embodiment.
Figure 5B:
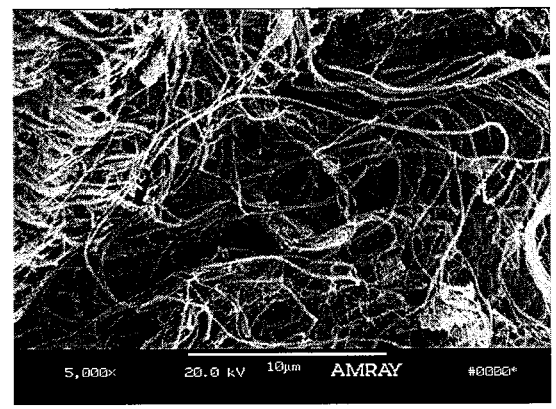

In yet a further embodiment, monolithic bone is demineralized and particulated before drying. Accordingly, the bone may be demineralized in monolithic pieces. The demineralized monolithic pieces may then be milled in a wet condition and critical point dried, for example using carbon dioxide as a medium. FIGS. 5a and 5b illustrate demineralized bone fibers and their nanofibrous surface structures, respectively, of demineralized bone matrix fiber processed in accordance with this embodiment.

Figure 6A:
FIG. 6a illustrates demineralized bone matrix wherein the bone has been demineralized, pressed, and then critical point dried, in accordance with one embodiment.
Figure 6B:
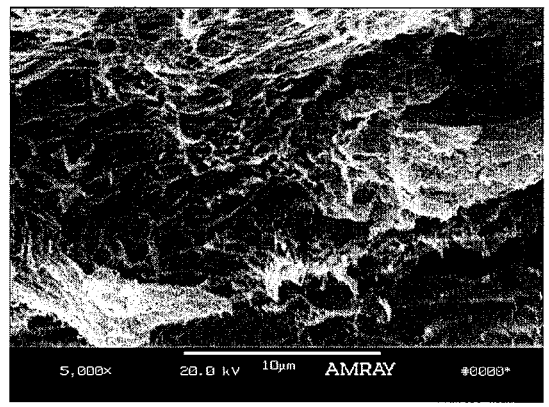

In yet a further embodiment, monolithic bone is demineralized and dried before particulating (if done). Accordingly, the bone may a demineralized in monolithic pieces. The DBM is pressed in a wet condition and then critical point dried, for example using carbon dioxide as a medium. FIGS. 6a and 6b illustrate demineralized bone matrix fibers and their nanofibrous surface structures, respectively, prepared in accordance with this embodiment. In alternatives of this embodiment, the demineralized and dried monolithic bone is not particulated and is processed as a monolithic implant.

Figure 4:
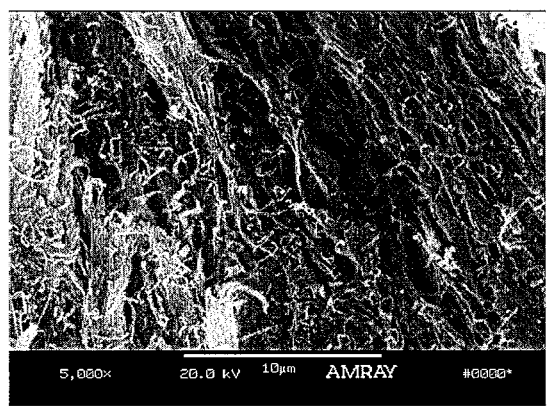
FIG. 4 illustrates the textured surface of demineralized bone matrix wherein the bone has been demineralized, lyophilized, and then milled in dry conditions, in accordance with one embodiment.

As noted, lyophilization and other methods of drying bone destroy the nanoscale texture on the exterior surface of the bone. The interior of the bone, however, may retain nanoscale texture. Thus, in some embodiments, methods disclosed herein expose the nanoscale texture in the interior of lyophilized, demineralized bone matrix. Specifically, in such embodiments, monolithic bone matrix may be demineralized and lyophilized. The demineralized, lyophilized bone matrix is then milled to obtain demineralized particles from the interior of the bone matrix. FIG. 4 illustrates surface of such processed demineralized bone matrix. As shown, the surface of the bone particles is nanofibrous. Thus, this embodiment exposes interior nanofibrous structures of a demineralized monolithic bone matrix to surface after milling. Milling may be done to particulate the bone in a fibrous manner or in a particle manner.

In other embodiments, the bone matrix is dried using lyophilization and nanoscale textured surface is imparted to the bone matrix as described below.

In accordance with various embodiments, the bone compositions provided herein may have neutral and polar lipid content below approximately 5% before defatting and demineralizing.

V. Impart Nanofibrous Structure to Bone Matrix

In some embodiments, nanostructures may be imparted to the bone to provide or enhance a nanoscale textured surface. Thus, for example, in some embodiments, the bone matrix may be processed in a typical manner wherein the nanoscale textured surface is compromised and nanostructures may be imparted to the bone matrix. In other embodiments, bone matrix having a nanoscale textured surface, such as bone matrix processed using CPD, may have further nanostructures imparted thereto to enhance the nanoscale textured surface.

In accordance with embodiments wherein nanostructures are imparted to the bone matrix, collagen, polylactide nanostructures, or other nanostructure materials may be added to the surface of bone matrix. Such nanostructures may include, for example, nanofibers, nanoparticles, nanopores, nanospheres or nanomicelles. The nanostructures can be prepared before or during incorporation process. Any suitable manner of associating the nanostructure materials with the bone matrix may be used including, for example, adsorption, coating, precipitation, phase separation, self-assembly, electrospinning, etc.

In some embodiments, nanostructure materials added to the bone matrix may contain therapeutic factors that can promote cellular response and tissue regeneration or have other functional properties. The factors can be antibiotics, functional peptides, proteins, growth factors, cytokines, DNAs, RNAs, siRNAs and the combination of those.

In one embodiment, imparting nanostructures to bone matrix may be done by coating or precipitating a nanostructure material on the bone matrix, thereby providing or enhancing a nanoscale textured surface of the bone matrix. In various embodiments the nanostructure material may be naturally occurring or may be synthetic or may be a blend or mixture of naturally occurring and synthetic materials. Suitable naturally occurring materials include, for example, collagen, gelatin, alginate, hyaluronic acid, chitosan, other extracellular matrix components, and tissue extracts. Suitable synthetic materials include, for example, polymeric materials, bone minerals, apatite, hydroxyapatite, bioglass, and bioceramic-biopolymer nanocomposites. A further suitable material may be, for example, hydroxyapatite/chitosan (HAp/CTS). The nanostructure may have a uniform structure, a nonuniform structure, a fibrous structure, a nanoporous structure, a nano-scale roughness, or other structure. In some embodiments, the nanostructures may have a diameter of approximately 1-2 µm. In various embodiments, the nanostructure may be approximately 1 nm to approximately 1000 nm in at least one dimension. For example, the nanostructure may be approximately 40 nm to approximately 600 nm, from 50 nm to approximately 500 nm, from approximately 100 to approximately 400 nm, or other suitable size.

Figure 7A:
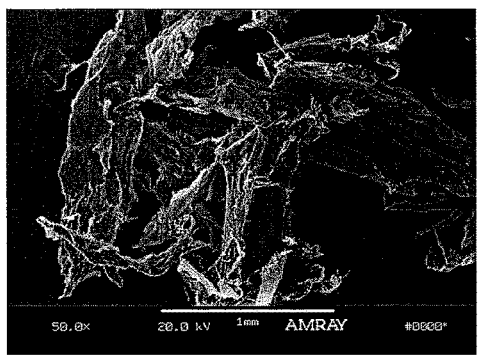
FIG. 7a illustrates collagen coated lyophilized demineralized bone matrix fibers, in accordance with one embodiment.
Figure 7B:
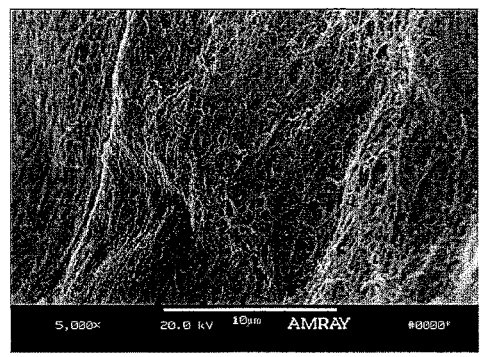

Thus, in some embodiments, naturally derived biomacromolecules such as collagen and gelatin may be used to form a nanoscale textured surface on the DBM. The nanostructure material may be imparted to, or placed on, the bone matrix in any suitable manner. In some embodiments, the DBM is mixed with a collagen or gelatin solution. The mixture is gelled and dried using lyophilization or critical point drying techniques. The resulting DBM can be cross-linked, for example using a chemical such as glutaraldehyde. Properties of the nanoscale textured surface provided by the nanostructures may be adjusted, for example by concentration of polymer, gelation conditions (temperature, pH, solvent), and cross-linking parameters. FIG. 7 illustrates demineralized bone matrix fibers and their nanofibrous surface, respectively, of DBM fibers wherein nanofibrous collagen has been applied to the DBM by coating/precipitation, in accordance with one embodiment.

Figure 8A:
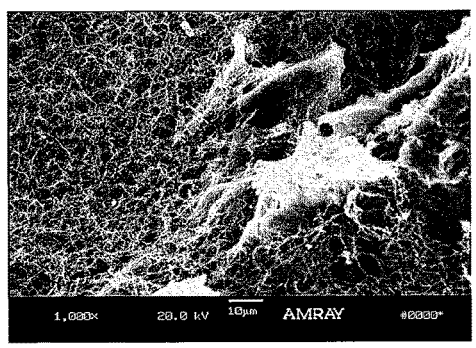
FIG. 8a illustrates poly(lactide) coated lyophilized demineralized bone matrix fibers, in accordance with one embodiment.
Figure 8B:
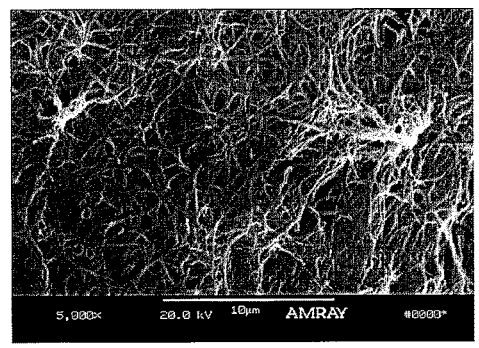

In another embodiment, imparting a nanoscale textured surface to bone matrix may be done by phase separation of a synthetic polymer. A typical biodegradable synthetic polymer, poly(L-lactide), is phase separated in tetrahydrofuran (THF) to introduce a nanofibrous coating on DBM. The phase separation temperature and polymer concentration are varied to adjust the density and morphology of the polymer surface coating. The polymer coating process can be performed either on typically-processed DBM having a compromised surface (e.g., lyophilized and having a smear layer and/or no nanoscale textured on the surface) or DBM with a nanoscale textured surface (e.g., critical point dried). FIGS. 8a and 8b illustrate DBM fibers and their surface, respectively, after adding nanofibrous poly(L-lactide) by coating and phase separation techniques. Adding nanostructures to the bone matrix substantially increase the surface area of the bone matrix. Such increased surface area may facilitate regulation of protein adsorption and cellular activity.

In yet other embodiments, imparting a nanoscale textured surface to bone matrix may be done by electrospinning nanofibers, such as polymer nanofibers, onto a DBM surface. In an example embodiment electrospinning of nanofibers, a high voltage is applied to a polymer solution, which overcomes the surface tension to form a charged jet. The charged polymer solution is ejected, dried, and solidified onto a grounded substrate, in this case, a DBM substrate in thin sheet form. The ejected polymer solutions repel each other to form thin fibers. By controlling the spinning conditions, the resulting fibers can range from about 0.02 µm to about 20 µm. A variety of polymers can be electrospun onto DBM surface. The polymers include biodegradable synthetic polymers such as poly(lactide) (PLLA), poly(lactide-co-glycolide) (PLGA), polycaprolactone (PCL), poly(L-lysine), etc. and naturally derived polymers such as collagen, gelatin, chitosan, hyaluronic acid, alginate, etc.

In yet other embodiments, imparting nanostructures to a surface of a bone matrix may be done by self-assembling nanostructures onto the DBM surface. Self-assembly refers to a spontaneous organization of individual molecules into a well-defined structure with noncovalent interactions. DBM comprises collagen and other non-collagenous proteins or biomacromolecules. The biomacromolecules in DBM may be treated to form surfaces with charged cationic ($—NH_3^+$) or anionic ($—COO^-$) polyelectrolytes or with different hydrophilic and hydrophobic domains. Biomacromolecules with opposite charges or hydrophilic/hydrophobic properties are then immobilized onto the DBM surface. Under certain conditions, the immobilized biomolecules form nanostructures. The biomacromolecules for nanostructure self-assembly can be polypeptides, oligopeptides, peptide-maphiphiles, or synthetic diblock/triblock polymers and dendrimers.

In yet other embodiments, biologically active factors may be incorporated into the nanostructures which are imparted onto the DBM surfaces. The biologically active factors may be compounds with low molecular weight or macromolecules with high molecular weight including proteins, cytokines, growth factors, enzymes, DNA, RNAs, and others. Suitable compounds include, for example, those described with respect to Optional Additives, below. In one embodiment, macromolecules form nanostructures on the surface of the DBM, for example via self-assembly. In another embodiment, the factors are dissolved or dispended in a solution of materials which form nanostructures on the DBM surfaces, for example via electrospinning, coating, precipitation, or other mechanism. In yet another embodiment, factors are encapsulated into polymer nanoparticles using a double emulstion technique wherein biological factors are encapsulated by the polymer nanoparticles. The nanoparticles may then be provided on the DBM, for example via coating. The nanostructure imparted onto the DBM surface provides a controlled delivery approach for the biologically active molecules.

Further, in some embodiments, the embodiments described above may be applied to a bone matrix wherein the nanofibrous structure has not been compromised. For example, a nanofibrous coating may be applied to a bone matrix wherein the nanofibrous structure has not been compromised.

VI. Whitening or Lightening the Bone Matrix

In accordance with some embodiments, a method is provided for whitening bone or DBM without exposure to bleach or peroxide. Specifically, $CO_2$ may be used as asolvent for lipids or lipidphilic substances. Removing lipids or lipidphilic substances from the bone matrix results in a lightened or whitened bone matrix. Thus, in methods using critical point $CO_2$ for drying the bone matrix, the bone may be whitened.

VII. Optional Additives

In accordance with various embodiments, the bone matrix provided herein may be used with growth factors, extracts, peptide hormones, or other additives to increase the osteoinductive capacity or that otherwise encourage cell or biological activity of the bone matrix or to impart other benefits to the bone matrix. As may be appreciated, in some embodiments, an additive may be encapsulated in the nanostructure imparted to the bone matrix. It will be appreciated that the amount of additive used will vary depending upon the type of additive, the specific activity of the particular additive preparation employed, and the intended use of the composition. The desired amount is readily determinable by the user.

The nanoscale textured surface of the bone compositions provided herein aids in growth factor retention and controlled release, cell attachment, and osteoconductivity of the bone matrix. It also imparts a larger surface area to the bone. The larger surface area can affect protein adsorption. Further, the interaction between nanofibers and additives affects the release kinetics of additives from matrix. The imparted nanoscale textured surface may provide additional growth factor release mechanism for bone matrix.

Any of a variety of medically and/or surgically useful optional substances can be incorporated in, or associated with, the osteoinductive factors either before, during, or after preparation of the osteoinductive or biologically active composition. Thus, for example when demineralized bone particles are used to form the material, one or more of such substances may be introduced into the demineralized bone particles, for example, by soaking or immersing the bone particles in a solution or dispersion of the desired substance(s).

Medically/surgically useful substances that can be readily combined with the DBM include, for example, collagen, insoluble collagen derivatives, etc., and soluble solids and/or liquids dissolved therein, e.g., antiviricides, particularly those effective against HIV and hepatitis; antimicrobials and/or antibiotics such as erythromycin, bacitracin, neomycin, penicillin, polymyxin B, tetracyclines, viomycin, chloromycetin and streptomycins, cefazolin, ampicillin, azactam, tobramycin, clindamycin and gentamicin, etc.; biocidal/biostatic sugars such as dextroal, glucose, etc.; amino acids, peptides, vitamins, inorganic elements, cofactors for protein synthesis; hormones; endocrine tissue or tissue fragments; synthesizers; enzymes such as collagenase, peptidases, oxidases, etc.; polymer cell scaffolds with parenchymal cells; angiogenic drugs and polymeric carriers containing such drugs; collagen lattices; antigenic agents; cytoskeletal agents; cartilage fragments, living cells such as chondrocytes, bone marrow cells, mesenchymal stem cells, natural extracts, tissue transplants, bone, demineralized bone powder, autogenous tissues such blood, serum, soft tissue, bone marrow, etc.; bioadhesives, bone morphogenic proteins (BMPs), angiogenic factors, transforming growth factor (TGF-beta), insulin-like growth factor (IGF-1); growth hormones such as somatotropin; bone digestors; antitumor agents; immuno-suppressants; permeation enhancers, e.g., fatty acid esters such as laureate, myristate and stearate monoesters of polyethylene glycol, enamine derivatives, alpha-keto aldehydes, etc.; and, nucleic acids. The amounts of such optionally added substances can vary widely with optimum levels being readily determined in a specific case by routine experimentation.

In one embodiment, a tissue-derived extract may be added to the bone matrix. U.S. patent application Ser. No. 12/140,044 discloses such extracts and addition of such extracts to DBM and is incorporated herein by reference. For example, a tissue-derived extract or partially demineralized bone may be added to the bone matrix. The extract may be derived from any suitable tissue, such as bone, bladder, kidney, brain, skin, or connective tissue. Further, the extract may be derived in any suitable manner. The extract may be allogeneic, autogeneic, xenogeneic, or transgenic. In embodiments wherein the extract is bone-derived, the bone may be cortical, cancellous, or corticocancellous and may be demineralized, partially demineralized, or mineralized. In some embodiments, the extract may comprise demineralized bone, partially demineralized bone, mineral derived from bone, or collagen derived from bone. In some embodiments, the tissue-derived extract may be a protein extract.

Bone regeneration involves a multitude of cells (e.g. cartilage, fibroblasts, endothelial, etc.) besides osteoblasts. Stem cells may be combined with the bone matrix. Accordingly, the bone matrix composition may be used to deliver stem cells, which offers the potential to give rise to different types of cells in the bone repair process. In one embodiment, the bone matrix composition further comprises a cell such as an osteogenic cell or a stem cell. In various embodiments, the additive may comprise radiopaque substances, angiogenesis promoting materials, bioactive agents, osteoinducing agents, or other. Reference is made to U.S. patent application Ser. Nos. 11/555,606 and 11/555,608, herein incorporated by reference, for specific discussion of possible additives.

In certain embodiments, the additive is adsorbed to or otherwise associated with the bone matrix. The additive may be associated with the bone matrix through specific or non-specific interactions, or covalent or noncovalent interactions. Examples of specific interactions include those between a ligand and a receptor, an epitope and an antibody, etc. Examples of nonspecific interactions include hydrophobic interactions, electrostatic interactions, magnetic interactions, dipole interactions, van der Waals interactions, hydrogen bonding, etc. In certain embodiments, the additive is attached to the bone matrix composition, for example, to the carrier, using a linker so that the additive is free to associate with its receptor or site of action in vivo. In other embodiments the additive is either covalently or non-covalently attached to the carrier. In certain embodiments, the additive may be attached to a chemical compound such as a peptide that is recognized by the carrier. In another embodiment, the additive is attached to an antibody, or fragment thereof, that recognizes an epitope found within the carrier. In certain embodiments at least additives are attached to the osteoimplant. In other embodiments at least three additives are attached to the osteoinductive or biologically active composition. An additive may be provided within the osteoinductive or biologically active composition in a sustained release format. For example, the additive may be encapsulated within biodegradable polymer nanospheres, microspheres, etc.

Any suitable method for adding, or dispersing, the additive to the bone matrix may be used. Generally, the procedures used to formulate or disperse the additive onto the bone matrix are sensitive to the physical and chemical state of both the additive and the bone matrix.

VIII. Addition of Bone Matrix to Carrier

In various embodiments, the bone matrix provided herein may be combined, with or without additives, with a carrier or excipient to achieve consistency for specific uses. For example, a carrier may be selected to provide the bone matrix composition in a gel consistency, a putty consistency, a matrix consistency, or other to form an osteoinductive or biologically active composition. The osteoinductive or biologically active composition may be configured to be moldable, extrudable, or substantially solid. The osteoinductive or biologically active composition may be configured to substantially retain its shape in water for a period of time. The osteoinductive or biologically active composition may form an osteoimplant useful in clinical applications. Suitable carriers may include surface demineralized bone; mineralized bone; nondemineralized cancellous scaffolds; demineralized cancellous scaffolds; cancellous chips; particulate, demineralized, guanidine extracted, species-specific (allogenic) bone; specially treated particulate, protein extracted, demineralized, xenogenic bone; collagen; synthetic hydroxyapatites; synthetic calcium phosphate materials; tricalcium phosphate, sintered hydroxyapatite, settable hydroxyapatite; polylactide polymers; polyglycolide polymers, polylactide-co-glycolide copolymers; tyrosine polycarbonate; calcium sulfate; collagen sheets; settable calcium phosphate; polymeric cements; settable poly vinyl alcohols, polyurethanes; resorbable polymers; and other large polymers; liquid settable polymers; and other biocompatible settable materials. The carrier may further comprise a polyol (including glycerol or other polyhydroxy compound), a polysaccharide (including starches), a hydrogel (including alginate, chitosan, dextran, pluronics, N,O-carboxymethyl-chitosan glucosamine (NOCC)), hydrolyzed cellulose, or a polymer (including polyethylene glycol). In embodiments wherein chitosan is used as a carrier, the chitosan may be dissolved using known methods including in water, in mildly acidic aqueous solutions, in acidic solutions, etc.

The carrier may further comprise a hydrogel such as hyaluronic acid, dextran, pluronic block copolymers of polyethylene oxide and polypropylene, and others. Suitable polyhydroxy compounds include such classes of compounds as acyclic polyhydric alcohols, non-reducing sugars, sugar alcohols, sugar acids, monosaccharides, disaccharides, water-soluble or water dispersible oligosaccharides, polysaccharides and known derivatives of the foregoing. An example carrier comprises glyceryl monolaurate dissolved in glycerol or a 4:1 to 1:4 weight mixture of glycerol and propylene glycol. Reference is made to U.S. Pat. No. 5,314,476 for other carriers including polyhydroxy carriers, to U.S. Pat. No. 6,884,778 for biocompatible macromere that may be used as carriers, and to U.S. Patent Publication No. 2003/0152548 for cross-linkable monomers that may be used as carriers, all herein incorporated by reference. Settable materials may be used, and they may set up either in situ, or prior to implantation. Optionally, xenogenic bone powder carriers also may be treated with proteases such as trypsin. Xenogenic carriers may be treated with one or more fibril modifying agents to increase the intraparticle intrusion volume (porosity) and surface area. Useful agents include solvents such as dichloromethane, trichloroacetic acid, acetonitrile and acids such as trifluoroacetic acid and hydrogen fluoride. The choice of carrier may depend on the desired characteristics of the composition. In some embodiments, a lubricant, such as water, glycerol, or polyethylene glycol may be added.

Any suitable shape, size, and porosity of carrier may be used. In some embodiments, the carrier may be settable and/or injectable. Such carrier may be, for example, a polymeric cement, a settable calcium phosphate, a settable poly vinyl alcohol, a polyurethane, or a liquid settable polymer. Suitable settable calcium phosphates are disclosed in U.S. Pat. Nos. 5,336,264 and 6,953,594, which are hereby incorporated by reference. Hydrogel carriers may additionally impart improved spatial properties, such as handling and packing properties, to the osteoconductive composition. An injectable carrier may be desirable where the composition is used with a containment device. In addition, selected materials must be biocompatible in vivo and optionally biodegradable. In some uses, the carrier acts as a temporary scaffold until replaced by new bone. Polylactic acid (PLA), polyglycolic acid (PGA), and various combinations have different dissolution rates in vivo. In bone, the dissolution rates can vary according to whether the composition is placed in cortical or trabecular bone.

The carrier may comprise a shape-retaining solid made of loosely adhered particulate material, e.g., with collagen. It may alternatively comprise a molded, porous solid, a monolithic solid, or an aggregate of close-packed particles held in place by surrounding tissue. Masticated muscle or other tissue may also be used. Large allogenic bone implants may act as a carrier, for example where their marrow cavities are cleaned and packed with DBM and, optionally, the osteoinductive factors.

One way to protect small size particles from cellular ingestion and/or to provide a diffusion barrier is to embed them in a monolithic bioabsorbable matrix, and then fragment the particle-containing monolithic matrix into particle sizes greater than 70 microns, for example, greater than 100 microns, or greater than 150 microns in their smallest dimension. Suitable matrices for embedding DBM compositions include biocompatible polymers and setting calcium phosphate cements. Generally the DBM composition/polymer weight ratio will range from about 1:5 to about 1:3. In the case of calcium phosphate, the DBM may be present up to 75% by weight. In one embodiment, bone matrix is embedded in a resorbable polymer. In a further embodiment, bone matrix particles are embedded in one of the setting calcium phosphates known to the art.

The carrier may comprise a number of materials in combination, some or all of which may be in the form of fibers and/or particles. The carrier may comprise calcium phosphates. Driessens et al. "Calcium phosphate bone cements," Wise, D. L., Ed., *Encyclopedic Handbook of Biomaterials and Bioengineering, Part B, Applications* New York: Marcel Decker; Elliott, *Structure and Chemistry of the Apatites and Other Calcium Phosphates* Elsevier, Amsterdam, 1994, each of which is incorporated by reference. Calcium phosphate matrices include, but are not limited to, dicalcium phosphate dihydrate, monetite, tricalcium phosphate, tetracalcium phosphate, hydroxyapatite, nanocrystalline hydroxyapatite, poorly crystalline hydroxyapatite, substituted hydroxyapatite, and calcium deficient hydroxyapatites.

In one embodiment, the carrier comprises an osteoinductive material such as a mineralized particulated material, osteoinductive growth factors, or partially demineralized bone. The mineralized particulated material may be TCP, hydroxyapatite, mineral recovered from bone, cancellous chips, cortical chips, surface demineralized bone, or other material. The osteoinductive material may be combined with a further carrier such as starch or glycerol. Accordingly, in some embodiments, the bone matrix may act as a carrier for the tissue-derived extract.

The bone matrix composition may be completely insoluble or may be slowly solubilized after implantation. Following implantation, the composition may resorb or degrade, remaining substantially intact for at least one to seven days, or for two or four weeks or longer and often longer than 60 days. The composition may thus be resorbed prior to one week, two weeks, three weeks, or other, permitting the entry of bone healing cells.

IX. Formation of an Implant

The bone matrix compositions provided herein may be used to form an osteoinductive or biologically active osteoimplant, such as an implant that has surfaces that encourage cell or biological activity. The osteoimplant resulting from the bone matrix, additive, and/or carrier may be flowable, have a putty consistency, may be shaped or molded, and/or may be deformable. The osteoimplant may assume a determined or regular form or configuration such as a sheet, plate, disk, tunnel, cone, or tube, to name but a few. Prefabricated geometry may include, but is not limited to, a crescent apron for single site use, an I-shape to be placed between teeth for intra-bony defects, a rectangular bib for defects involving both the buccal and lingual alveolar ridges, neutralization plates, reconstructive plates, buttress plates, T-buttress plates, spoon plates, clover leaf plates, condylar plates, compression plates, bridge plates, or wave plates. Partial tubular as well as flat plates can be fabricated from the osteoimplant. Such plates may include such conformations as, e.g., concave contoured, bowl shaped, or defect shaped. The osteoimplant can be machined or shaped by any suitable mechanical shaping means. Computerized modeling can provide for the intricately-shaped three-dimensional architecture of an osteoimplant custom-fitted to the bone repair site with great precision. In embodiments wherein the osteoimplant is shaped or moldable, the implant may retain coherence in fluids.

Accordingly, the osteoinductive or biologically active bone matrix composition may be subjected to a configuring step to form an osteoimplant. The configuring step can be employed using conventional equipment known to those skilled in the art to produce a wide variety of geometries, e.g., concave or convex surfaces, stepped surfaces, cylindrical dowels, wedges, blocks, screws, and the like. A surgically implantable material fabricated from elongated bone particles that have been demineralized according to the invention, which may be shaped as a sheet, and processes for fabricating shaped materials from demineralized bone particles is disclosed in U.S. Pat. Nos. 5,507,813 and 6,436,138, respectively, the contents of which are herein incorporated by reference. Suitable sheets include those sold under the trade name Grafton® DBM Flex, which must be wetted/hydrated prior to use to be useful for implantation. Such sheets have recently been reported as effective in seeding human bone marrow stromal cells (BMSCs), which may be useful in the repair of large bone defects. Kasten et al., "Comparison of Human Bone Marrow Stromal Cells Seeded on Calcium-Deficient Hydroxyapatite, Betatricalcium Phosphate and Demineralized Bone Matrix," *Biomaterials,* 24(15):2593-603, 2003. Also useful are demineralized bone and other matrix preparations comprising additives or carriers such as binders, fillers, plasticizers, wetting agents, surface active agents, biostatic agents, biocidal agents, and the like. Some exemplary additives and carriers include polyhydroxy compounds, polysaccharides, glycosaminoglycan proteins, nucleic acids, polymers, polaxomers, resins, clays, calcium salts, and/or derivatives thereof.

In some embodiments, the osteoinductive or biologically active bone matrix composition may be placed in a containment device such as a porous mesh to provide a delivery system. In various embodiments, the device may comprise a polymer (such as polyalkylenes (e.g., polyethylenes, polypropylenes, etc.), polyamides, polyesters, polyurethanes, poly(lactic acid-glycolic acid), poly(lactic acid), poly(glycolic acid), poly(glaxanone), poly(orthoesters), poly(pyrolicacid), poly(phosphazenes), L-co-G, etc.), other bioabsorbable polymer such as Dacron or other known surgical plastics, a natural biologically derived material such as collagen, a ceramic (with bone-growth enhancers, hydroxyapatite, etc.), PEEK (polyether-etherketone), dessicated biodegradable material, metal, composite materials, a biocompatible textile (e.g., cotton, silk, linen), or other. In one embodiment, the containment device is formed as a long bag-like device and may be used with minimally invasive techniques.

In some embodiments, the osteoinductive or biologically active bone matrix composition may be combined with a carrier such as a polymer carrier and molded into a solid implant. U.S. Pat. Nos. 6,696,073, 6,478,825, 6,440,444, and 6,294,187 and U.S. Patent Publications Nos. 2006/0216323 and 2005/0251267, which are hereby incorporated by reference for all purposes, disclose such implants and methods for making such implants.

X. Formulation of Bone Matrix Containing Compositions

The osteoinductive or biologically active bone matrix composition, the carrier, or the osteoimplant may be formulated for a particular use. The formulation may be used to alter the physical, biological, or chemical properties of the carrier. A physician would readily be able to determine the formulation needed for a particular application, taking into account such factors as the type of injury, the site of injury, the patient's health, and the risk of infection. In various embodiments, the composition may comprise, for example less than approximately 0.5% water, less than approximately 1% water, or less than approximately 5% water.

Osteoinductive or biologically active bone matrix compositions, carriers, or osteoimplants therefore may be prepared to have selected resorption/loss of osteoinductivity rates, or even to have different rates in different portions of an implant. For example, the formulation process may include the selection of partially demineralized particles of a particular size or composition, combined with the selection of a particular stabilizing agent or agents, and the amounts of such agents.

Physical properties such as deformability and viscosity of the carrier may also be chosen depending on the particular clinical application. The bone matrix provided herein may be mixed with partially demineralized bone and/or other materials and factors to improve other characteristics of the implant. For example, the bone matrix may be mixed with other agents to improve wound healing. These agents may include drugs, proteins, peptides, polynucleotides, solvents, chemical compounds, and biological molecules.

Further, the bone matrix composition may be formulated to be settable and/or injectable. Thus, for example, the composition may be injectable through a 10-gauge, a 12-gauge, or an 18-gauge needle.

Accordingly, in some embodiments the bone matrix composition may be rubbery, rubbery with chunks, stiff (as freeze-dried), stiff with chunks, putty, paste, flowable, or injectable. The term "flowable" in this context applies to compositions whose consistencies range from those which can be described as shape-sustaining but readily deformable, e.g., those which behave like putty, to those which are runny. Specific forms of flowable bone powder compositions include cakes, pastes, creams and fillers. Reference is made to U.S. Pat. No. 5,290,558, herein incorporated by reference in its entirety, for discussion of flowable materials.

Also, as previously discussed, the osteoinductive or biologically active bone matrix composition may be formed into various shapes and configurations, including rods, strings, sheets, weaves, solids, cones, discs, fibers, and wedges. Such shapes may result from a monolithic bone piece or an aggregate of bone particles. In certain embodiments, the shape and size of the bone matrix affect the time course of osteoinductivity. For example, in a cone or wedge shape, the tapered end will result in osteoinductivity shortly after implantation of the osteoimplant, whereas the thicker end will lead to osteoinductivity later in the healing process (hours to days to weeks later). In certain embodiments, bone matrix osteoimplants may include an aggregate of bone particles, the particles have a length of greater than 2 mm, greater than 1.5 mm, greater than 1 mm, greater than 500 microns, or greater than 200 microns across its widest dimension. Also, larger particle size will induce bone formation over a longer time course than smaller particles. Particles of different characteristics (e.g., composition, size, shape) may be used in the formation of these different shapes and configurations. For example, the osteoimplant may include a sheet of partially demineralized bone, with a layer of long half-life particles alternated between layers of shorter half-life particles. See U.S. Pat. No. 5,899,939, herein incorporated by reference, for suitable examples. In a weave, strands composed of short half-life particles may be woven together with strands of longer half-lives.

XI. Conclusion

Bone matrix compositions and, more specifically, bone matrix compositions having nanofibrous structures and methods for their production are provided. In various embodiments, the bone matrix compositions comprise demineralized bone, partially demineralized bone, surface demineralized bone, or non-demineralized bone. In accordance with some embodiments, a DBM composition is provided wherein greater than about 1%, about 10%, about 20%, about 30%, about 40%, about 50%, about 60%, about 70%, about 80%, about 90%, or about 99% of the DBM particles have nanofibrous structures. In accordance with some embodiments, mineralized or surface demineralized bone is provided wherein greater than about 1%, about 10%, about 20%, about 30%, about 40%, about 50%, about 60%, about 70%, about 80%, about 90%, or about 99% of the particles have nanofibrous structures. In accordance with some embodiments, bone matrix having a predetermined moisture content, for example, about 15%, about 8%, about 6%, about 3%, or about 1%, and having greater than about 40%, about 50%, about 60%, about 70%, about 75%, about 80%, about 90%, or about 99% non-denatured collagen are provided. In accordance with yet other embodiments, compositions are provided comprising bone matrix and extract wherein the particle surfaces are at least greater than approximately 20% nanofibrous in nature. The nanofibrous structures may be provided by processing the bone such that the native nanofibrous structure of the bone is maintained. In other embodiments, the nanofibrous structure may be imparted to the bone by adding nanofibrous materials to the bone.

Although the invention has been described with reference to specific embodiments, persons skilled in the art will recognize that changes may be made in form and detail without departing from the spirit and scope of the invention.

What is claimed is:

1. A method for producing a demineralized bone matrix composition comprising: providing bone; demineralizing the bone; drying the bone such that collagen fibrils on a surface of the bone are compromised; adding a hydrogel carrier and adding nanostructures via electrospinning to the bone to provide a nanoscale textured surface.

2. The method of claim 1, wherein adding nanostructures to the bone comprises adding collagen to the bone.

3. The method of claim 1, wherein adding nanostructures materials to the bone comprises adding polylactide nanofibers to the bone.

4. The method of claim 1, wherein adding nanostructures to the bone comprises adding collagen, polylactide, polycaprolactone, polyglycolide, chitosan, gelatin, or other nanofibrous material to the bone.

5. The method of claim 4, wherein the nanofibrous materials include an encapsulated biological active molecule.

6. The method of claim 1, wherein the hydrogel carrier comprises dextran, pluronics, or N,O-carboxymethylchitosan glucosamine (NOCC).

7. A method for producing a demineralized bone matrix composition, the method comprising providing bone; demineralizing the bone; drying the bone such that collagen fibrils on a surface of the bone are compromised and yield lyophilized demineralized bone particles; adding a hydrogel carrier and adding nanostructures to the lyophilized demineralized bone particles to provide a nanoscale textured surface comprising collagen nanofibers electrospun onto the lyophilized demineralized bone particles, wherein the imparted surface includes at least 60% non-denatured collagen, wherein the composition has less than about 15% moisture content, wherein the nanoscale textured surface comprises nanostructures each having a length ranging from approximately 40 nm to approximately 600 nm.

* * * * *